US010422895B2

(12) United States Patent
Hong et al.

(10) Patent No.: US 10,422,895 B2
(45) Date of Patent: Sep. 24, 2019

(54) PASSIVE WAVEGUIDE STRUCTURES AND INTEGRATED DETECTION AND/OR IMAGING SYSTEMS INCORPORATING THE SAME

(71) Applicant: The Trustees of Princeton University, Office of Technology and Trademark Licensing, Princeton, NJ (US)

(72) Inventors: Lingyu Hong, Princeton, NJ (US); Kaushik Sengupta, Princeton, NJ (US)

(73) Assignee: The Trustees of Princeton University, Office of Technology and Trademark Licensing, Princeton, NJ (US)

(*) Notice: Subject to any disclaimer, the term of this patent is extended or adjusted under 35 U.S.C. 154(b) by 0 days.

(21) Appl. No.: 15/431,304

(22) Filed: Feb. 13, 2017

(65) Prior Publication Data

US 2017/0153339 A1    Jun. 1, 2017

Related U.S. Application Data

(62) Division of application No. 14/570,590, filed on Dec. 15, 2014, now Pat. No. 9,568,619.

(Continued)

(51) Int. Cl.
*G01J 1/04* (2006.01)
*G01T 1/24* (2006.01)
(Continued)

(52) U.S. Cl.
CPC .............. *G01T 1/36* (2013.01); *G01J 1/0425* (2013.01); *G01J 1/0488* (2013.01);
(Continued)

(58) Field of Classification Search
None
See application file for complete search history.

(56) References Cited

U.S. PATENT DOCUMENTS 6,014,251 A * 1/2000 Rosenberg ............... G02B 5/20
                                                              343/909
8,554,027 B2 * 10/2013 Tokushima ............ B82Y 20/00
                                                              385/16

(Continued)

OTHER PUBLICATIONS

Jang et al., "A CMOS fluorescent-based biosensor microarray", Solid-State Circuits Conference—Digest of Technical Papers, 2009. ISSCC 2009. IEEE International, pp. 436-437,437a, Feb. 2009.
Huang et al., "A 0.18- \mu m CMOS Array Sensor for Integrated Time-Resolved Fluorescence Detection", Solid-State Circuits, IEEE Journal of, vol. 44, Issue 5, pp. 1644-1654, 2009.

(Continued)

*Primary Examiner* — Tina M Wong
(74) *Attorney, Agent, or Firm* — Moser Taboada

(57) ABSTRACT

Passive components adapted for integration with at least one active semiconductor device, in an embodiment, comprise at least one metallic structure dimensioned and arranged to absorb and/or reflect a major fraction of incident electromagnetic radiation received at one or more wavelengths of a first group of wavelengths. This prevents radiation within the first group of wavelengths from being received and/or processed by the at least one active device. In an embodiment, one or more metallic structures are dimensioned and arranged to direct an amount of incident radiation, received at one or more wavelengths of a second group of wavelengths, sufficient to enable receiving or processing of incident radiation within the second group of wavelengths by the at least one active semiconductor device. In some embodiments, the passive component comprises a passive optical filter for use in spectroscopic applications, and the active semiconductor device is a detector or sensor.

20 Claims, 21 Drawing Sheets

Related U.S. Application Data

(60) Provisional application No. 61/915,560, filed on Dec. 13, 2013.

(51) Int. Cl.

| | | |
|---|---|---|
| *G01T 1/36* | (2006.01) | |
| *G02B 1/00* | (2006.01) | |
| *G02B 6/10* | (2006.01) | |
| *G01N 21/64* | (2006.01) | |
| *G02B 6/122* | (2006.01) | |

(52) U.S. Cl.
CPC ..... *G01N 21/6454* (2013.01); *G01N 21/6458* (2013.01); *G01T 1/24* (2013.01); *G02B 1/002* (2013.01); *G02B 6/107* (2013.01); *G02B 6/1226* (2013.01)

(56) References Cited

U.S. PATENT DOCUMENTS

| | | | |
|---|---|---|---|
| 8,779,995 B2* | 7/2014 | Kirino | G01S 7/032 343/701 |
| 9,568,619 B2* | 2/2017 | Hong | G02B 1/002 |
| 2004/0041663 A1* | 3/2004 | Uchimura | H01P 1/2088 333/135 |
| 2005/0128028 A1 | 6/2005 | Sanchez et al. | |
| 2011/0150385 A1 | 6/2011 | Kornilovich | |
| 2014/0288541 A1 | 9/2014 | Eshkol et al. | |

OTHER PUBLICATIONS

Wang, et al., "A Frequency-Shift CMOS Magnetic Biosensor Array with Single-Bead Sensitivity and No External Magnet"; California Institute of Technology, Pasadena, California; 2009 IEEE International Solid-State Circuits Conference, ISSCC 2009/ Session 25/Medical/ 25.6, 3 pages.

Hall et al., "A 256 channel magnetoresistive biosensor microarray for quantitative proteomics", VLSI Circuits (VLSIC), 2011 Symposium on, pp. 174-175, Jun. 2011.

Yokogawa, et al., "Plasmonic Color Filters for CMOS Image Sensor Applications", Thomas J. Watson Laboratories of Applied Physics, California Institute of Technology, Pasadena, California; ACS Publications 2012 American Chemical Society, pp. 4349-4354.

Field et al., "A 100-fps fluorescence lifetime imager in standard 0.13-$\mu$m CMOS", VLSI Circuits (VLSIC), 2013 Symposium on, pp. C10-C11, Jun. 2013.

Lee et al., "An on-chip 72×60 angle-sensitive single photon image sensor array for lens-less time-resolved 3-D fluorescence lifetime imaging", VLSI Circuits Digest of Technical Papers, 2014 Symposium on, pp. 1-2, Jun. 2014.

Pai, et al., "A handheld magnetic sensing platform for antigen and nucleic acid detection"; Department of Electrical Engineering, California Institute of Technology, Pasadena, California; Department of Electrical and Computer Engineering, Georgia Institute of Technology, Atlanta, Georgia; The Royal Society of Chemistry, Analyst, 2014, pp. 1403-1411.

Hong et al., "A fully integrated CMOS fluorescence biosensor with on-chip nanophotonic filter", VLSI Circuits (VLSI Circuits), 2015 Symposium on, pp. C206-C207, Jun. 2015.

\* cited by examiner

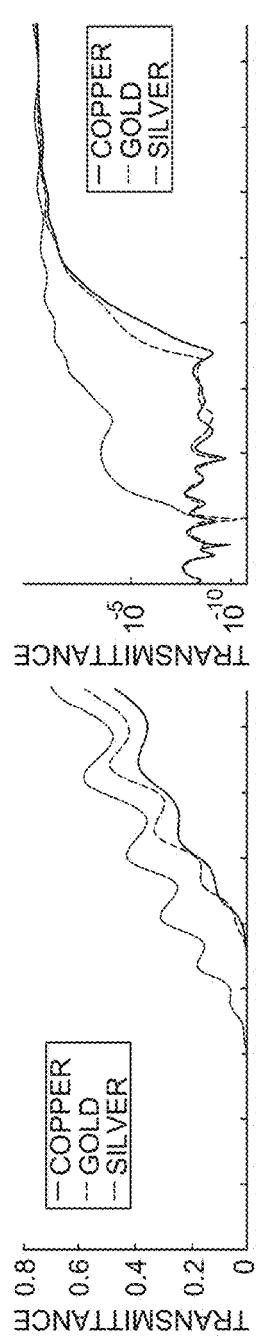
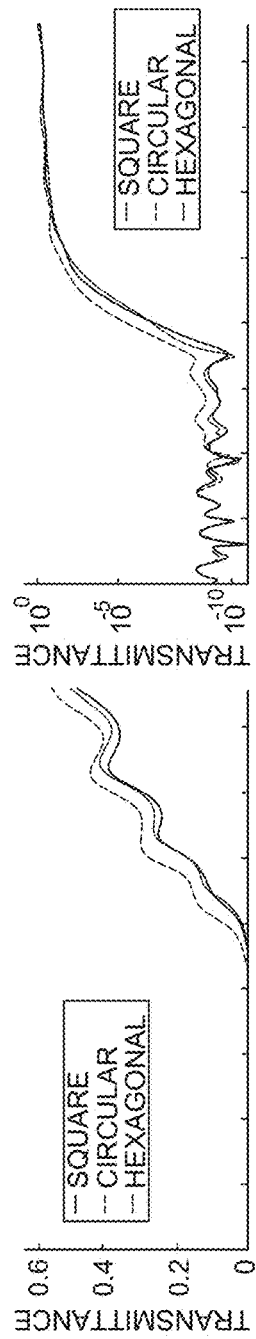
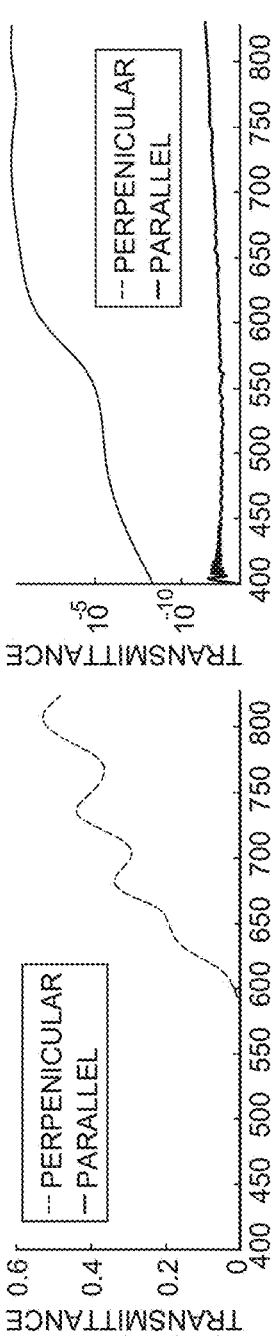
FIG. 3A  FIG. 3B  FIG. 3C  FIG. 3D  FIG. 3E  FIG. 3F

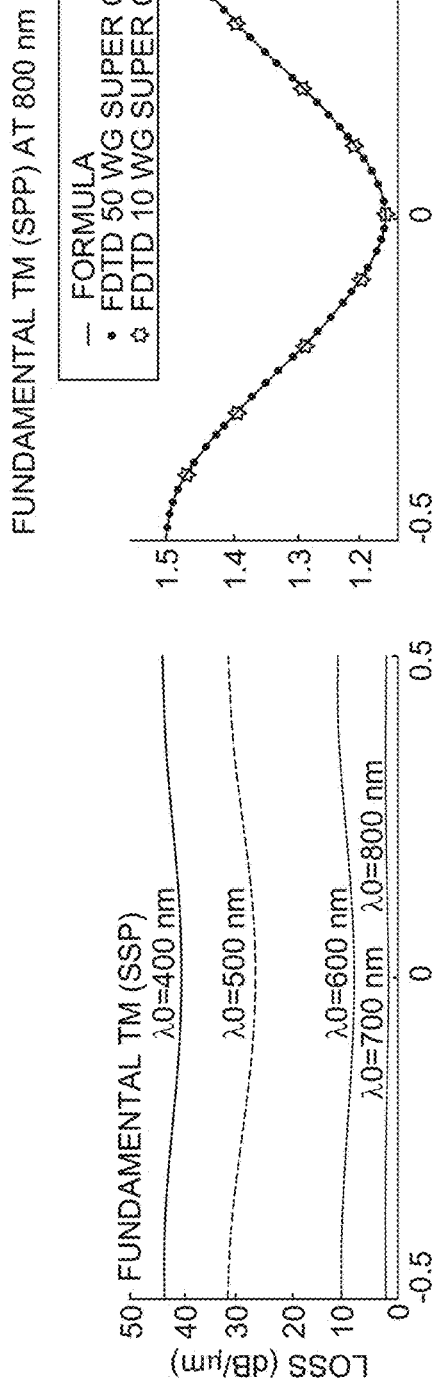
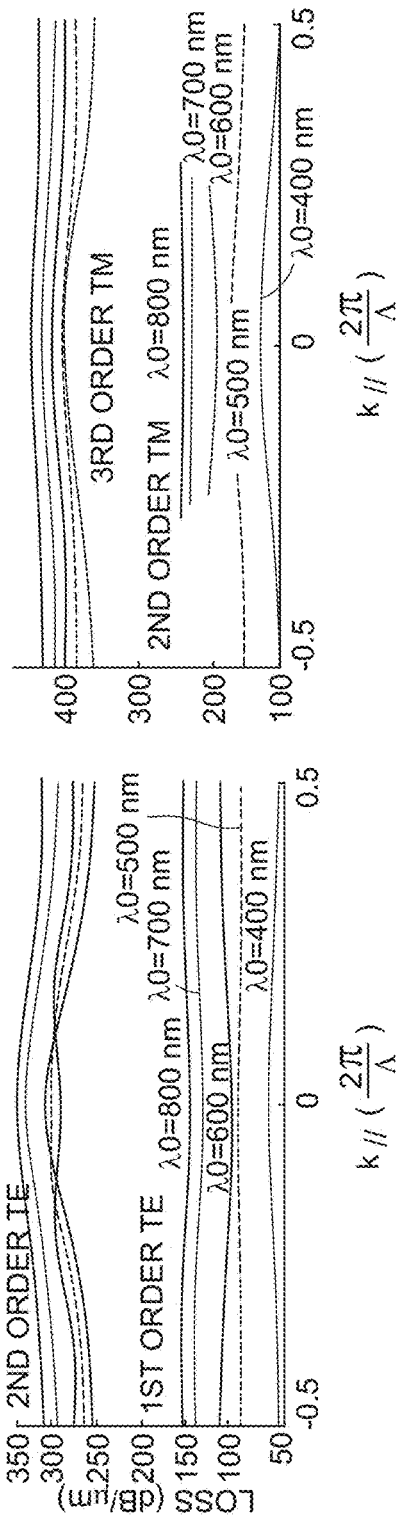
FIG. 5B
FIG. 5C
FIG. 5D
FIG. 5E

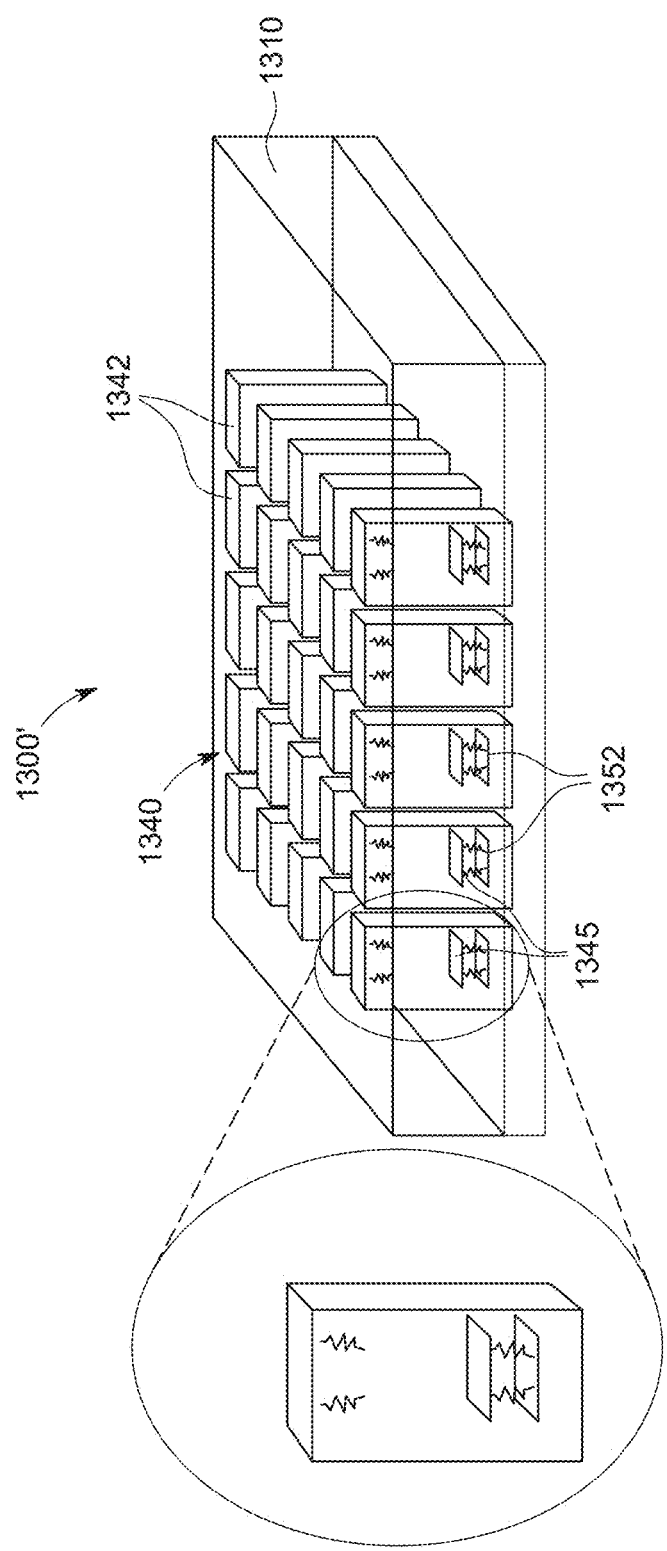

PASSIVE WAVEGUIDE STRUCTURES AND INTEGRATED DETECTION AND/OR IMAGING SYSTEMS INCORPORATING THE SAME

REFERENCE TO RELATED APPLICATIONS

This application is a divisional of U.S. patent application Ser. No. 14/570,590 filed Dec. 15, 2014 which claims benefit of priority to Provisional Application Ser. No. 61/915,560 filed on Dec. 13, 2013

BACKGROUND OF THE INVENTION

Field of the Invention

Conventional detection and/or imaging systems are used to detect, sense and/or measure properties of light over a portion of the electromagnetic spectrum. A spectrometer, for example, typically includes a source of electromagnetic energy as well as a collimating lens structure and optical filter configured to disperse the light to electronic photodetectors such as a CMOS active pixel sensor array, an array of photodiodes, or charge-coupled devices (CCDs).

Optical spectroscopic systems are used to detect and quantify the characteristics or concentration of a physical, chemical, or biological target object. Medical diagnostic machines using optical spectroscopic systems can identify pathogens and chemicals in bodily fluids, as well track associated enzymes, proteins, and other physiological responses to such items, using only minute samples of blood, urine, saliva, or the like. Heretofore, however, the expense, size and complexity associated with conventional optical spectroscopic systems have impeded their widespread deployment. This, only those laboratory facilities having elaborate testing protocols and specially trained technicians are able to analyze specimens using such machines. As a consequence, the time required to deliver samples to the lab, the costs associated with shipping, and the handling procedures designed to avoid misidentification and/or contamination, have further limited the range of diagnostic options available to medical practitioners.

A continuing need therefore exists for detecting and/or imaging systems which are efficient, easy to use, and relatively inexpensive to fabricate and maintain.

SUMMARY OF THE INVENTION

The Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

A passive component according to one or more embodiments is adapted for integration with at least one active semiconductor device. The passive component comprises at least one metallic structure dimensioned and arranged to absorb and/or reflect a major fraction of incident electromagnetic radiation received at one or more wavelengths of a first group of wavelengths, so as to prevent such major fraction of incident radiation from being one of received or processed by the at least one active device. Alternatively, or in addition, the at least one metallic structure is dimensioned and arranged to direct an amount of incident radiation, received at one or more wavelengths of a second group of wavelengths, sufficient to enable receiving or processing of incident radiation, within the second group of wavelengths, by the at least one active device.

A detection and/or sensing system according to one or more embodiments comprises at least one active component defined on a first substrate, the at least one active component comprising a semiconductor device dimensioned and arranged to at least one of detect or process radiation incident thereon. The system further comprises at least one passive component defined on a substrate, the at least one passive component including one or more metallic structures dimensioned and arranged to at least one of absorb or reflect a major fraction of incident radiation, the incident radiation received at one or more wavelengths of a first group of wavelengths, so as to prevent such major fraction of incident radiation from being one of received or processed by the at least one active component. Alternatively, or in addition, the at least one metallic structure is dimensioned and arranged to direct an amount of incident radiation, received at one or more wavelengths of a second group of wavelengths, sufficient to enable receiving or processing of incident radiation, within the second group of wavelengths, by the at least one active component.

According to one or more embodiments, the at least one metallic structure comprises a waveguide array filter, a grating array filter, or a meta material filter. In some embodiments, the at least one metallic structure alternatively or additionally includes a metallic lens structure formed from a plurality of metallic segments or rings defined in one or more layers of dielectic materials.

A monolithically integrated fluorescence detection system, comprising: a substrate of semiconductor material having a plurality of active components fabricated thereon, the active components including at least one of a plurality of sensing devices or a plurality of detector devices fabricated thereon; and a plurality of passive components formed thereon, at least some of the passive components being respectively dimensioned and arranged to receive radiation exiting a corresponding analyte and to direct the radiation along a path terminating at one or more of the sensing or detector devices, wherein each passive component comprises at least one metallic structure dimensioned and arranged to absorb and/or reflect a major fraction of received exiting radiation, received at one or more wavelengths of a first group of wavelengths, so as to prevent such major fraction from being one of received or processed by the plurality of sensing devices and/or plurality of detecting device. Alternatively, or in addition, the at least one metallic structure is dimensioned and arranged to direct an amount of received exiting radiation, received at one or more wavelengths of a second group of wavelengths, sufficient to enable at least one of receiving or processing by the at least one of the plurality of sensing devices or plurality of detecting devices.

BRIEF DESCRIPTION OF THE DRAWINGS

FIGS. 3A and 3B are graphical representation of transmittance as a function of wavelength for an illustrative sub-wavelength waveguide array structure according to an embodiment of the present disclosure, for each of three different metals used in their fabrication;

FIGS. 3C and 3D are graphical representations of transmittance as a function of wavelength for a illustrative sub-wavelength waveguide array structure according to an embodiment of the present disclosure, based on selection of copper as the metal used in their fabrication;

FIGS. 3E and 3F are graphical representations of transmittance as a function of wavelength for a illustrative sub-wavelength waveguide array structure according to an embodiment of the present disclosure, based on selection of copper as the metal used in their fabrication;

FIGS. 5B-5E depict distinct loss behaviors between two different kinds of modes for passive components employing an array of metallic structures according to one or more embodiments;

FIG. 13B is a schematic of a functionalized, monolithically integrated fluorescence imaging system constructed according to another embodiment of the present disclosure;

Figure 1A:
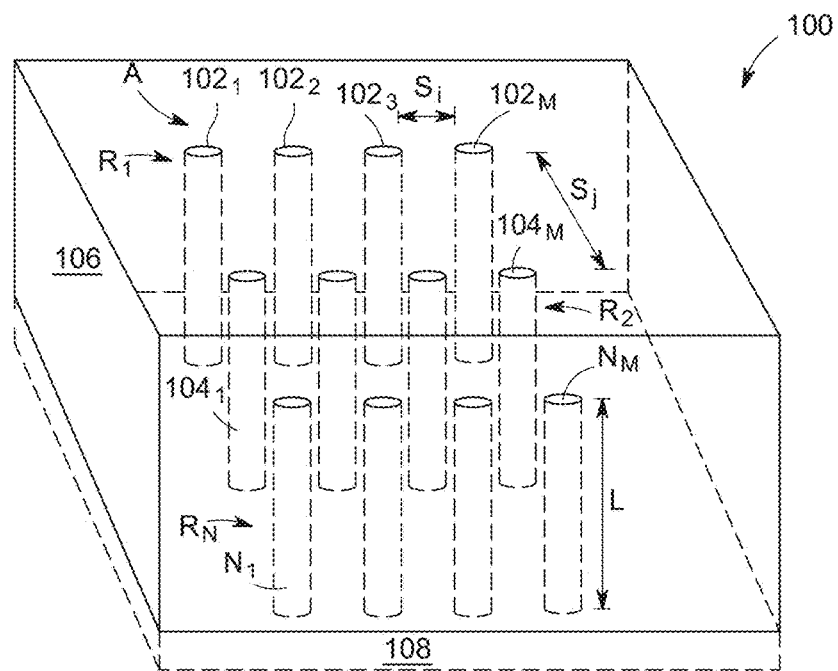
FIG. 1A is a perspective view of a passive component incorporating an array of metallic waveguides disposed within a dielectric layer, according to one or more embodiments.

While the components and systems are described herein by way of example for several embodiments and illustrative drawings, it should be understood that the drawings and detailed description thereto are not intended to limit embodiments to the particular form disclosed. Rather, the intention is to cover all modifications, equivalents and alternatives falling within the spirit and scope of the components and systems defined by the appended claims. Any headings used herein are for organizational purposes only and are not meant to limit the scope of the description or the claims. As used herein, the word "may" is used in a permissive sense (i.e., meaning having the potential to), rather than the mandatory sense (i.e., meaning must). Similarly, the words "include", "including", and "includes" mean including, but not limited to.

DETAILED DESCRIPTION OF EMBODIMENTS

In the following detailed description, numerous specific details are set forth in order to provide a thorough understanding of the disclosure and how it may be practiced in particular embodiments. However, it will be understood that the present disclosure may be practiced without these specific details. In other instances, well-known methods, procedures and techniques have not been described in detail, so as not to obscure the present disclosure. While the present disclosure will be described with respect to particular embodiments and with reference to certain drawings, the disclosure is not limited hereto. The drawings included and described herein are schematic and are not limiting the scope of the disclosure. It is also noted that in the drawings, the size of some elements may be exaggerated and, therefore, not drawn to scale for illustrative purposes.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein. As used herein, the phrase major fraction is intended to refer not to a specific proportion, or even a range of percentage values of absorbtion and/or reflection of light, but rather to the rejection of a sufficient amount of energy as to impede the sensing, measuring, or detection of a energy at a particular wavelength or within a particular band of wavelengths other than those being reflected or absorbed.

As used herein, the phrase "dimensioned and arranged for silicon device integration" or "for semiconductor device integration" is intended to refer metallic components which are of a sufficiently small scale as to permit fabrication of spectral filters and other passive components made of metal (or a metal alloys during the process of fabricating one or more active devices within or upon a substrate of semiconductor material as, for example, silicon, gallium arsenide, indium gallium arsenide, or indium gallium arsenic phosphide (InGaAsP). In some embodiments, portions of the metallic structures comprising the passive components have dimensions on the order of 100 nm or even less.

As used herein, the term "metal material" structures are intended to refer to waveguide structures utilizing a gap or "slot", whether as discrete individual structures or as arrays of such individual structures, with the terms "slotted resonators" being one example thereof and intended to refer generically to such structures as the split ring resonator structures, and to "U" and "H" shaped resonator structures described in the present disclosure.

As used herein, the term "active component" is intended to refer to those devices fabricated from silicon or other semiconductor materials, especially but not limited to those fabricated from low cost CMOS fabrication processes, and which are responsive to the application of a current or voltage to alter the flow of current or the voltage applied to other devices in a circuit.

Described herein are passive components adapted for integration with a wide range of detection, sensing, and spectroscopic imaging devices. Although examples described in detail herein are presented in the context of novel optical fluorescence-based chemical and biochemical sensors and multi-analyte detection and imaging systems, such examples are presented to highlight the applicability of low-cost materials and simple fabrication techniques to the implementation of such systems. In the context of such illustrative examples set forth in this disclosure, an analyte is an element or a substance to be detected, such as a gas, a vapor or a liquid.

According to some embodiments of the present disclosure, passive components in the form of spectral filters and other metallic structures are respectively constructed as part of a conventional semiconductor device fabrication integration process such, for example, as a CMOS fabrication process. An illustrative example of a passive component 100 incorporating an array A of such metallic structures is depicted in FIG. 1A. The array, indicated generally at A, comprises m×n metallic waveguides, where one or both of M and N are integers greater than one. In FIG. 1A, each of M and N are greater than 1 and these are arranged in respective rows $R_1$ to $R_N$. Each row, as row $R_1$ for example, therefore includes M metallic waveguides indicated generally at $102_1$ to $102_M$. Likewise, row $R_2$ includes waveguides $104_1$ to $104_M$, and row $R_N$ includes waveguides $N_1$ to $N_M$.

The waveguides of array A may be made of arbitrary shapes, and are surrounded by a dielectric layer indicated generally at 106. The spacing between each waveguide in a row, as waveguides $102_1$ and $102_2$ of row $R_1$, is represented by reference numeral $S_i$ while the spacing between waveguides an array is represented by reference numeral Sj. In periodic examples, the spacing between waveguides is constant within each row and the spacing between the rows is likewise constant. In such embodiments, the dimensions $S_i$ and $S_j$ may, but need not be, equal to one another. In that regard, the spacing between waveguides need not even be periodic. In any event, dielectric layer 106 is disposed on a substrate 108 which, may be an index-matching dielectric layer and/or may include one or more active semiconductor devices fabricated in or on the substrate.

The spacings $S_i$ and Sj are each sub-wavelength. That is, each of $S_i$ and $S_j$ have a dimension which is less than the wavelength in the dielectric layer $\lambda_0/n$, where $\lambda_0$ is the wavelength in vacuum and n is the dielectric constant of the dielectric layer). This constraint ensures that only efficiently conducted modes in the waveguide array (coupled surface plasmon polariton modes) are permitted, while the other types of the modes (for example, cavity modes) are cut-off. Such mode purification is especially useful for spectral filtering according to one or more embodiments.

It should be emphasized that surface plasmon polariton modes have distinct waveguide loss for different wavelengths depending on the material property of both metal and dielectric, when the optical waves are guided through the waveguide, spectral filtering function is realized. One distinct advantage of the waveguide array for spectral filtering is that light incident at any angle has to be converted to the coupled surface plasmon polariton modes in order to go through the optical structure. Therefore, for any incident angle, the spectral filtering function is preserved.

Figure 1B:
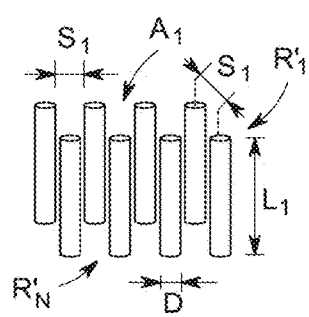
FIG. 1B is a perspective view depicting an array of metallic waveguides having a uniform spacing and pitch and a circular cross sectional profile, according to some embodiments.
Figure 1C:
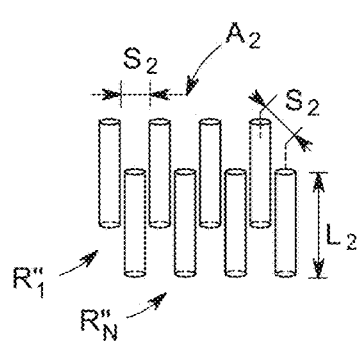
FIG. 1C is a perspective view depicting an array of metallic waveguides similar to that shown in FIG. 1B but having a hexagonal cross sectional profile, according to some embodiments.
Figure 1D:
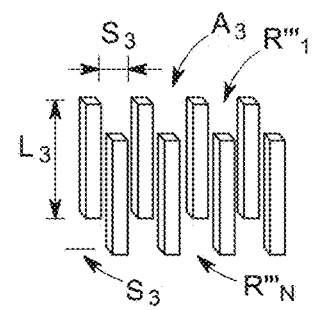
FIG. 1D is a perspective view depicting an array of metallic waveguides similar to that shown in FIGS. 1B and 1C but having a rectangular cross sectional profile, according to some embodiments.
Figure 2A:
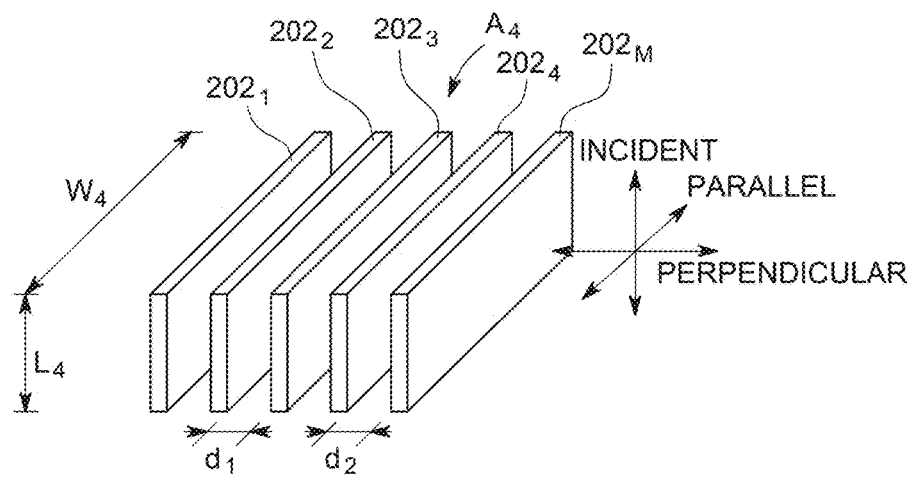
FIG. 2A is a perspective view of an array of metallic structures constructed according to one or more embodiments.
Figure 2B:
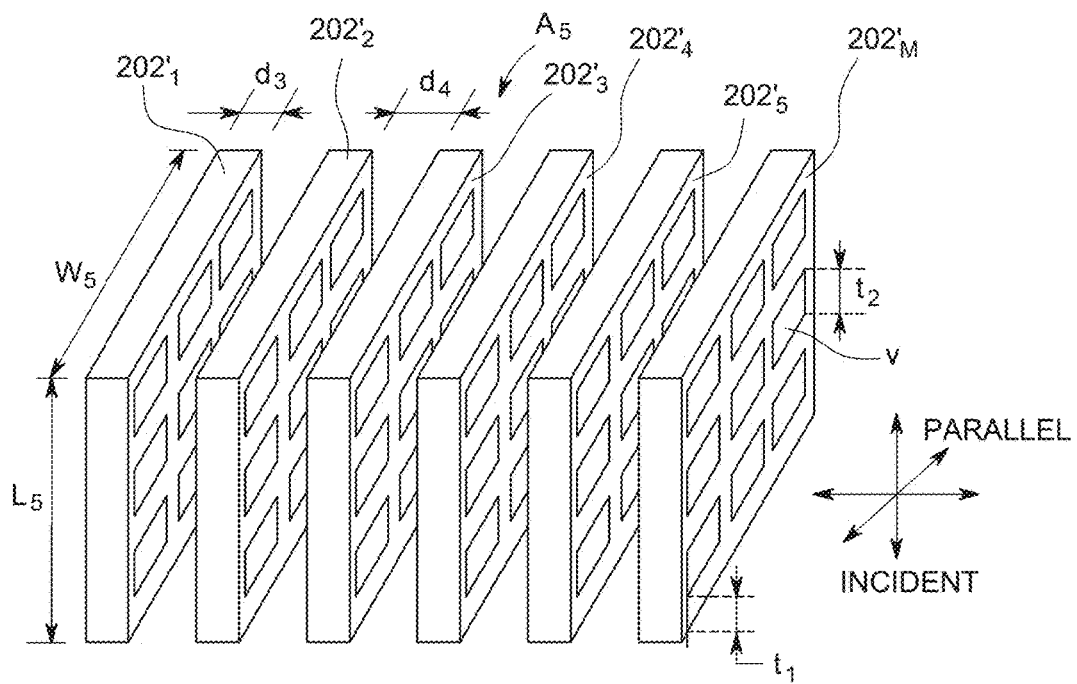
FIG. 2B is a perspective view of an array of metallic structures obtained by conventional CMOS fabrication techniques, according to one more embodiments.

The geometry of the sub-wavelength waveguide array can be chosen based on the convenience of the fabrication process, while the characteristics remain similar due to the fact that all sub-wavelength waveguide arrays share the same physics mentioned above. Various periodic waveguide arrays with the same material (e.g., Cu) but different waveguide unit cells (square, circular, hexagonal cross section), as shown in FIGS. 1D, 1B, and 1C, respectively, were simulated to demonstrate this behavior. It is also possible to design and fabricate one-dimensional (1×M) waveguide arrays as shown in FIGS. 2A and 2B (again, the spacing is sub-wavelength but the array doesn't have to be periodic). In the case of the array depicted in FIG. 2A, the filtering only exists for one polarization (perpendicular, as shown in the figure). For the parallel polarization, light for all wavelengths are largely rejected.

In practice, commercially available fabrication processes may requires specific design adaptations and conformance with rules applied to a specific geometric configuration. This may lead to many variants of the waveguide array as departures from the aforementioned basics structures. For example, a particular CMOS process may use leads to the design example shown as FIG. 2B, which is a variation to the basic design as FIGS. 1A and 2A, respectively. These structures, while seemingly complex, possess all the physical performance characteristics applicable to the generalized cases discussed above.

In an embodiment, a periodic waveguide array utilizes waveguides having a square cross section, as exemplified by FIG. 1D. Based on a length $L_3$ of 2 microns, a waveguide width of 100 nm, an inter-waveguide spacing $S_1$ of 100 nm, and a dielectric layer of $SiO_2$ (n~1.5), a simulation was performed to determine the transmittance characteristics as a function of material and the wavelengths making up the incident radiation (i.e., that portion of the electromagnetic spectrum which is incident upon the waveguides). FIG. 3A is a graphical representation of transmittance vs wavelength, for each of three different materials (the upper curve corresponding to silver, the middle curve corresponding to gold, and lower curve corresponding to copper). A similar plot, on a logarithmic scale, is depicted in FIG. 3B.

Selecting only copper for simulation purposes, waveguide arrays utilizing a periodic configuration and a circular cross section (FIG. 1B), a hexagonal cross section (FIG. 1C), and a square cross section (FIG. 1D) were also simulated, in all cases using $SiO_2$ (n~1.5) as the dielectric and a length ($L_1$, $L_2$ or $L_3$) of 2 microns. For waveguides having a circular cross sectional profile, a diameter D of 112.8 nm, and a spacing $S_1$ of 100 nm) were used, while in the case of the hexagonal cross sectional profile, the apical spacing was 76 nm and the side of each hexagon was 62.0 nm. FIG. 1D utilized the same parameters as discussed above in connection with FIG. 1D. A graphical plot of transmittance against wavelength is shown in FIG. 3C and, on a logarithmic scale, in FIG. 3D.

Figures 3G, 3H, 3I, 3J, 3K, 3L:
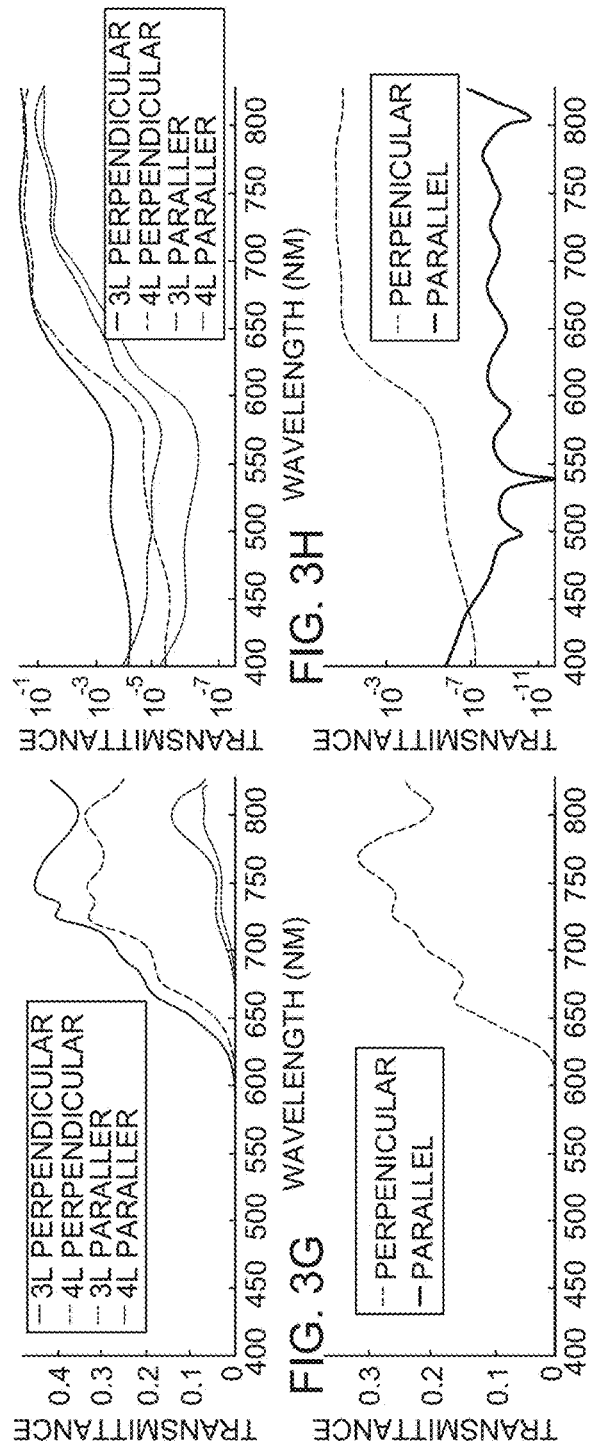
FIGS. 3G and 3H are graphical representations of transmittance as a function of wavelength for a illustrative sub-wavelength waveguide array structure according to an embodiment of the present disclosure, based on selection of copper as the metal used in their fabrication.
FIGS. 3I and 3J are graphical representations of transmittance as a function of wavelength for a illustrative sub-wavelength waveguide array structure according to an embodiment of the present disclosure, based on selection of copper as the metal used in their fabrication.
FIGS. 3K and 3L are graphical representations of transmittance as a function of wavelength for a illustrative sub-wavelength waveguide array structure according to an embodiment of the present disclosure, based on selection of copper as the metal used in their fabrication.

The simulated transmittance spectrum for a one-dimensional array structure of FIG. 2A, using copper in the fabrication of the waveguide structures, is shown in FIGS. 3E and 3F (logarithmic scale). For purposes of this simulation, a length $L_4$ of 2 microns, an infinite width $W_4$, an inter-waveguide spacing ($d_1=d_2$) of 100 nm, and an individual waveguide thickness of 100 nm were used. FIGS. 3K and 3L (logarithmic) also plots the angular dependency of filter performance for this structure, showing that the filter works for all angles of incidence, which is especially suited for fluorescence detection applications where the excitation light might be scattered and only obliquely entering the filter.

In FIGS. 3G and 3H (logarithmic), there is shown the spectrum for the structure depicted in FIG. 2B, which is denoted as having four layers ("4L") within each waveguide structure as structures $202'_1$ to $202'_M$, as well as the spectrum for the structure that only uses the metal 3 to metal 5 layers shown in FIG. 2B, this is denoted as "3L". In the simulation, the spacing $d_4$ between adjacent structures was 130 nm and the thickness $d_3$ of each structure was 100 nm. Each layer containing the vias, indicated generally at V, is 167 nm, while the metal layers have a thickness $t_1$ of 220 nm. Clearly, the "3L" is a shortened waveguide array structure compared to "4L", and therefore, its filtering performance is worse than that of the "4L", as expected—longer waveguides have better filtering performance, at the expense of slightly more loss at the desirable wavelength (in this case, the long wavelength at 800 nm).

Simulation results for a M×N comprising multiple rows of structures corresponding to the arrangement of FIG. 2B (not shown) is presented in FIGS. 3I and 3J (logarithmic), where M and N are each greater than 1.

Figure 4A:
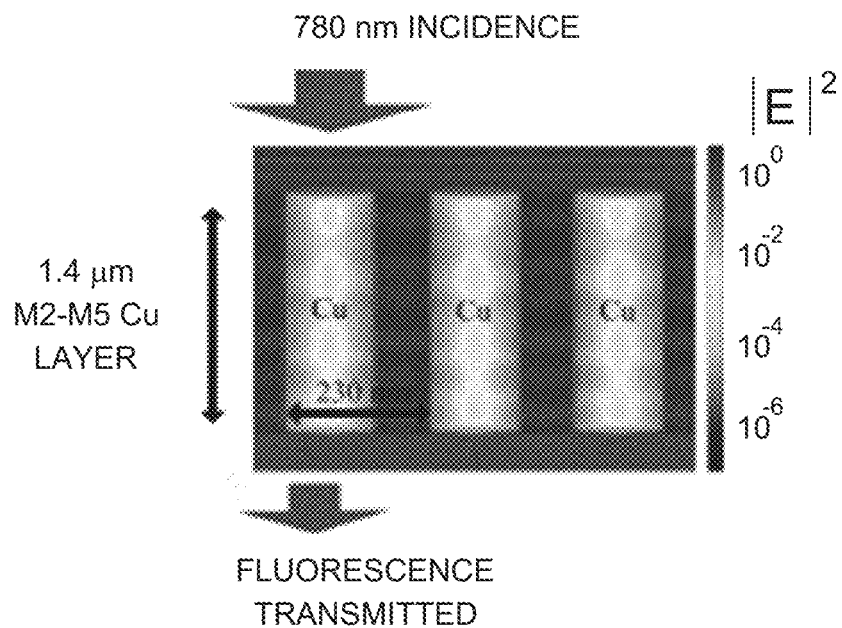
FIGS. 4A and 4B exemplify light of different wavelengths (780 nm and 405 nm, respectively) entering a spectral filter of the type employing an array of metallic waveguide structures according to the embodiments of FIGS. 1A-1D, 2A, and 2B.
Figure 4B:
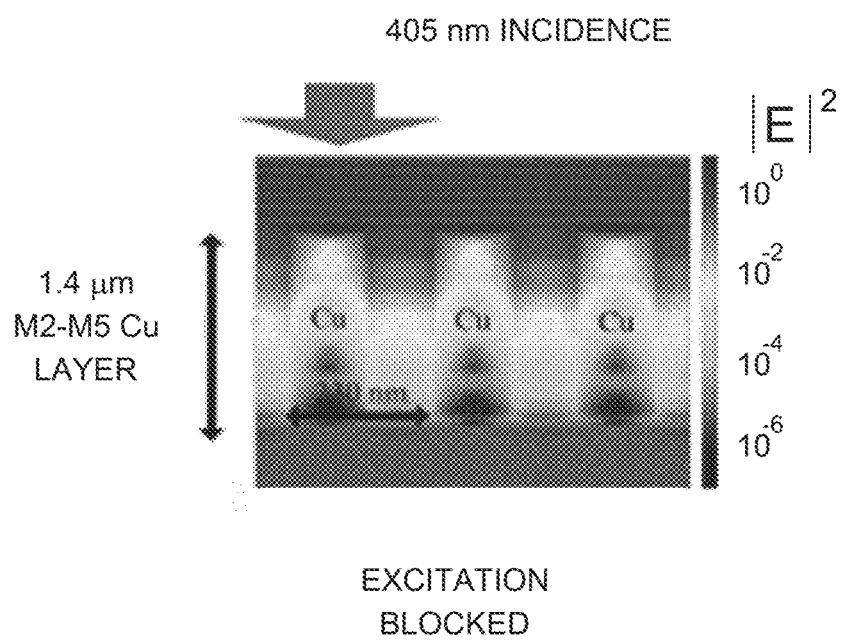
Figure 4C:
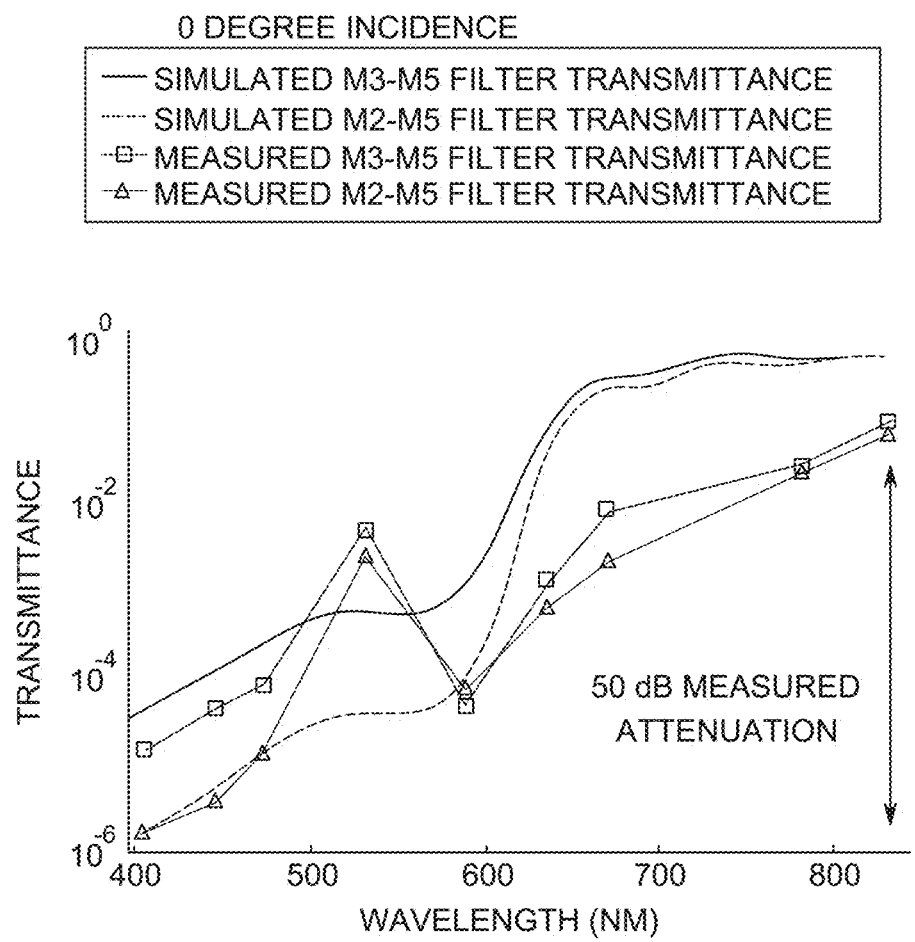
FIG. 4C is a graphical representation of the measured result (transmission spectrum) for a waveguide array designed and fabricated in a CMOS 65 nm process, according to one or more embodiments.
Figure 4D:
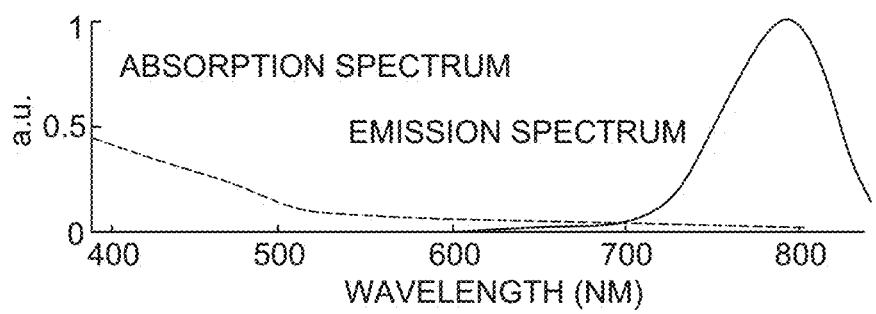
FIG. 4D is a graphical representation depicting filtering performance against the emission and excitation spectra for an exemplary commercial analyte, in accordance with a simulation of results achieved by one or more embodiments.

FIGS. 4A and 4B exemplify light of different wavelengths (780 nm and 405 nm, respectively) entering a spectral filter of the type employing an array of metallic waveguide structures according to the embodiments of FIGS. 1A-1D, 2A, and 2B. Comparing the two, it will be readily apparent that the 780 nm light largely passes through (e.g., without absorption and/or reflection) while the 405 nm is largely rejected The measured result (transmission spectrum) for a waveguide array designed and fabricated in a CMOS 65 nm process is shown in the FIG. 4C. The structure is the same as FIG. 2B. The simulated transmittances for a four-metal-layer filter (M2-M5) are −58.7 dB for 405 nm and −2.9 dB for 780 nm wavelength while the measured transmittances are −57.8 dB for 405 nm and −12.1 dB for 780 nm. The higher than expected propagation loss at 780 nm is currently being investigated. Nonetheless, a measured filtering ratio of 45.7 dB is achieved with the integrated nano-plasmonic filter. The filtering performance is plotted against the emission and excitation spectra (FIG. 4D) of the labeling agent Qdot 800 commercially available from Life Technologies, a quantum dot which is used in DNA as well as protein assays.

Figure 5A:
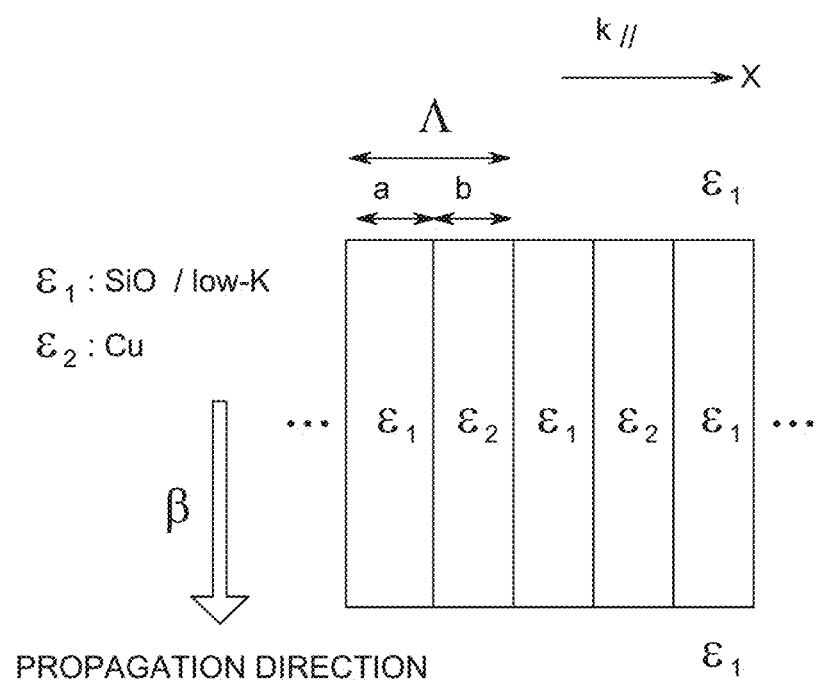
FIG. 5A is a model of coupled waveguide modes supported by filtering arrangements constructed in accordance with one or more embodiments.

A preliminary evaluation on the nanoplasmonic waveguide array system is carried out with the two-dimensional periodic waveguide array structure shown in FIG. 2B. All coupled waveguide modes supported in the system can be modeled as shown in FIG. 5A and described analytically by the following equations:

$$\cos k_{//} \Lambda - \cos(k_1 a)\cos(k_2 b) + \frac{1}{2}\left(\frac{\varepsilon_1}{\varepsilon_2}\frac{k_2}{k_1} + \frac{\varepsilon_2}{\varepsilon_1}\frac{k_1}{k_2}\right)\sin(k_1 a)\sin(k_2 b) = 0,$$

for TM $$\cos k_{//} \Lambda - \cos(k_1 a)\cos(k_2 b) + \frac{1}{2}\left(\frac{k_2}{k_1} + \frac{k_1}{k_2}\right)\sin(k_1 a)\sin(k_2 b) = 0,$$

for TE

Where $$k_1 = \sqrt{\varepsilon_1 k_0^2 - \beta^2},$$

$$k_2 = \sqrt{\varepsilon_2 k_0^2 - \beta^2}$$

Where, $k_0$ is the wave vector in vacuum, $\varepsilon_1$ is the dielectric constant of the dielectric layer, $\varepsilon_2$ is the dielectric constant of the metal layer, a is the width of the dielectric spacing, b is the width of the metal waveguide, $k_{//}$ is the parallel wave vector charactering the coupled surface plasmon mode and $\beta$ is the wave vector or propagation constant of the waveguide modes—which determines the loss of the waveguides for any particular wavelengths. Distinct behaviors between two different kinds of modes are clearly seen in FIGS. 5B-5E. The coupled surface plasmon polariton modes, which are also the fundamental coupled TM modes, serve as the filtering mechanism of the structure—with drastically larger mode loss in short wavelength (405 nm) than in long wavelength (780 nm). However, other modes (which behave like cut-off cavity modes) show larger mode loss for longer wavelength. These cut-off cavity modes could be a degradation sources for the filter, if the designed pitch of the filter is larger than ~300, while smaller pitch (~200 nm) design makes the effect negligible. This explains the function of the sub-wavelength spacing, mentioned above.

FIG. 6A-6D depict another class of metallic structures adapted for integration with such conventional devices as detectors and imaging sensors and which may, for example, be used to implement an optical filter or other passive optical component. In a CMOS embodiment, wherein the structure 600 is configured as an on-chip grating anomaly filter, the structure comprises a plurality of two dimensional metal grating stacks (the material is either copper or aluminum, depending on the CMOS process). In the illustrative embodiment of FIG. 6B, three such stacks, indicated generally at reference numerals 610, 620, and 630, are shown.

The filter of FIGS. 6A-6D is designed to reject, to a large extent, short wavelength light over a relatively small wavelength range (subject to tuning during the manufacturing process according to the selection of variable design parameters) and to allow longer wavelength light to pass efficiently. The filter works well particularly when the laser light incidence is normal to the filter plane. The pitch P of each two-dimensional grating in a stack (as gratings 610, 620 or 630 of FIG. 6B) is determined in accordance with Wood's anomaly law, wherein $$P = m \times \frac{\lambda_0}{n},$$

Where $\lambda_0$ is the wavelength of the laser in vacuum, n is the refractive index where the grating is embedded (in the case of CMOS chip, it's the oxide layer on the silicon substrate), and m is integer (m=1 is typically used). In an embodiment, the width of the grating is on the order of from about 0.5 to 0.7 times the pitch. The grating thickness is not as important a parameter as the pitch and width, especially for fluorescence sensing applications. Therefore, the thickness can be at the convenience of particular fabrication process that is used. Nonetheless, these three parameters are preferably optimized based on rigorous FDTD simulations. Although FIGS. 6A and 6B suggest the stacking of three gratings in parallel, a greater or larger number of gratings may be employed to obtain a requisite level of the filter performance.

There are generally two ways of cascading. First, multiple same 2D gratings can be cascaded in order to significantly enhance the laser rejection at a particular wavelength. Second, multiple two-dimensional gratings with slightly different pitches (say, 5-10 nm difference) can be cascaded to enhance the bandwidth of rejection. The enhanced bandwidth, in turn, allows the laser to incident within a certain angle (thus enhancing the robustness of the filter). In order for the cascading to be effective, the spacing between adjacent filter layers should be as large as possible, practically, to be around the laser wavelength in the dielectric medium.

Figure 6A:
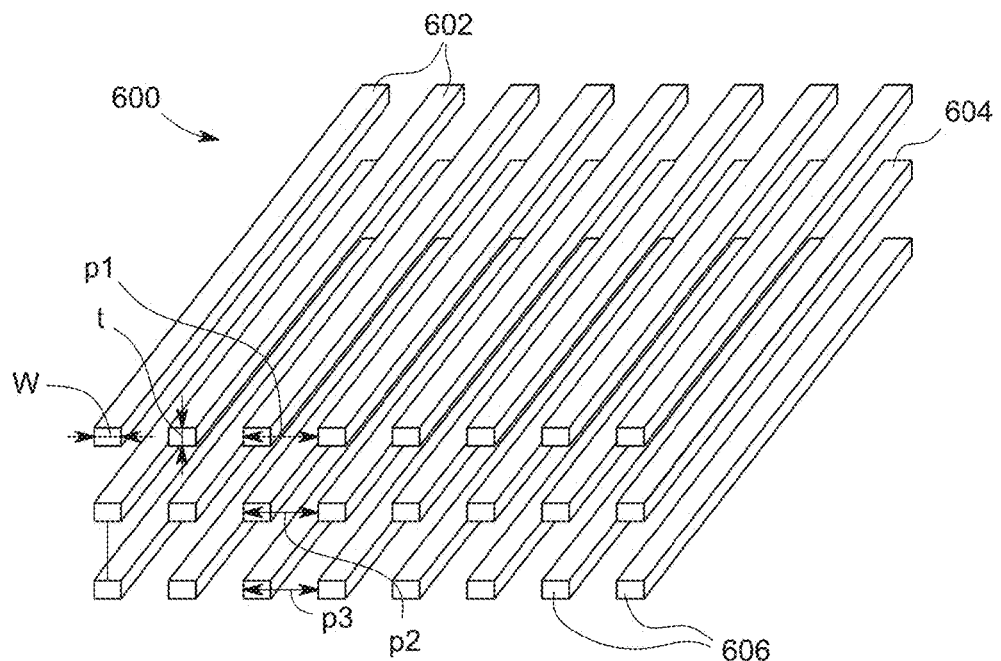
FIG. 6A-6B and depict another class of metallic structures adapted for integration with such conventional devices as detectors and imaging sensors and which may, for example, be used to implement grating anomaly filters or other passive optical components according to one or more embodiments.
Figure 6B:
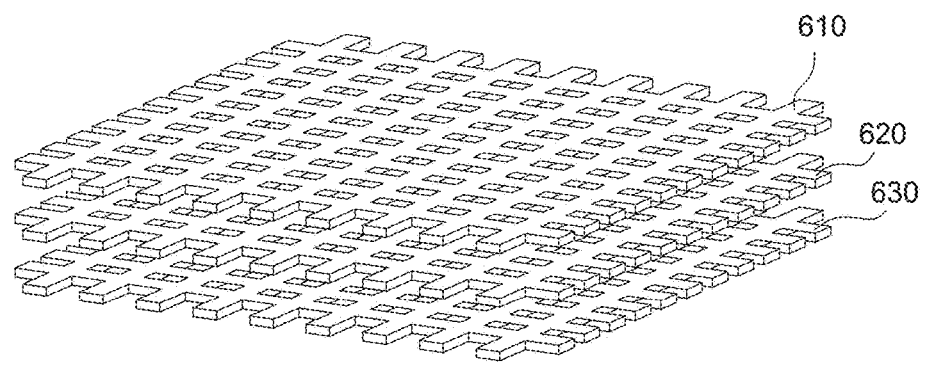
Figure 6C:
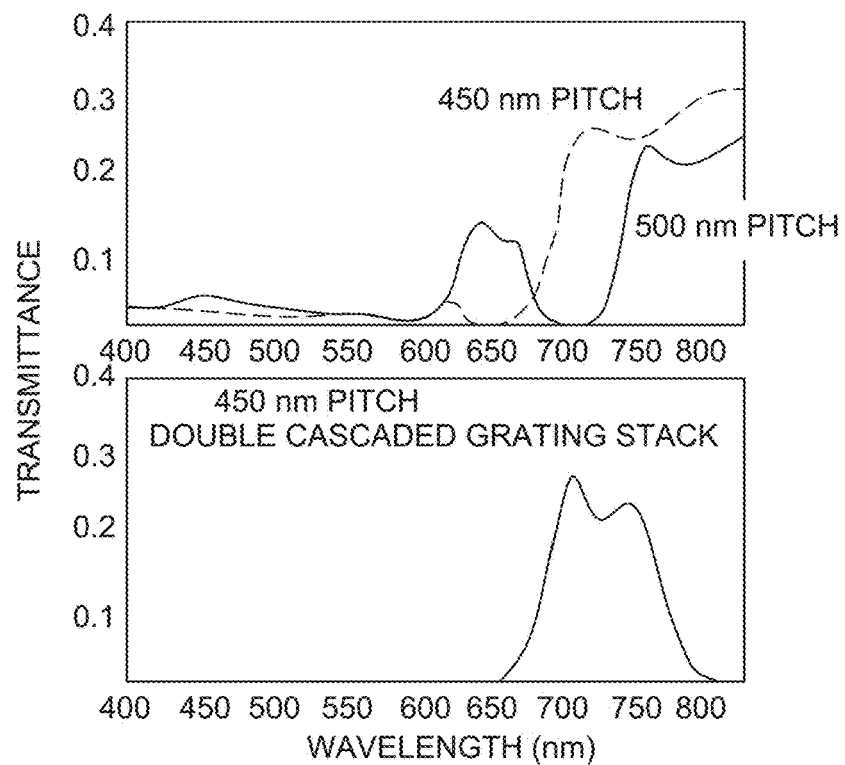
FIGS. 6C and 6D depict FDTD simulation results for several design examples of grating anomaly filters according to one or more embodiments of the present disclosure.
Figure 6D:
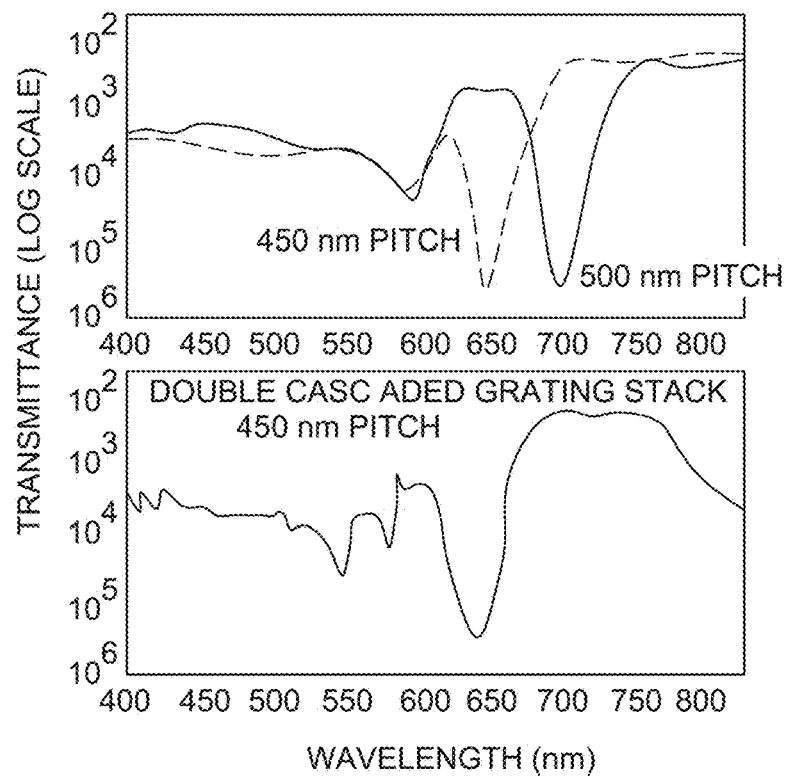

Several design examples are given and the corresponding FDTD simulation results are shown in FIGS. 6C and 6D. In each of the design examples, the grating material is chosen to be copper, though a noble metal such as gold, silver or platinum would also provide satisfactory results. The first and second grating examples are single layer two-dimensional gratings, each having a pitch of 450 nm, and 500 nm respectively. The thicknesses of the films are both t=220 nm, the widths are W=270 nm and 300 nm, respectively. The refractive index of the dielectric medium is assumed to be 1.35. The third grating is a cascaded design-two 450 nm pitch single grating layers are positioned in parallel with a spacing of 1 micron. It can be seen that the 450 nm pitch grating exhibits anomaly wavelength ru·mmd 650 nm, and the 500 nm pitch grating around 710 nm, which is a very desirable property (wavelength to be filtered is controllable). The transmission dip at the anomaly wavelength is on the order of around $10^{-3}$ to $10^{-4}$. Although this is already a typical value found in traditional multiple-dielectric-layer-based or absorptive-material-based filters, if cascading is applied, the rejection at the anomaly wavelength is cascaded ($10^{-6}$ to $10^{-7}$ transmittance), as shown in the bottom of FIG. 6D. This enables high signal-to-noise ratio in fluorescence detection applications.

Figure 7A:
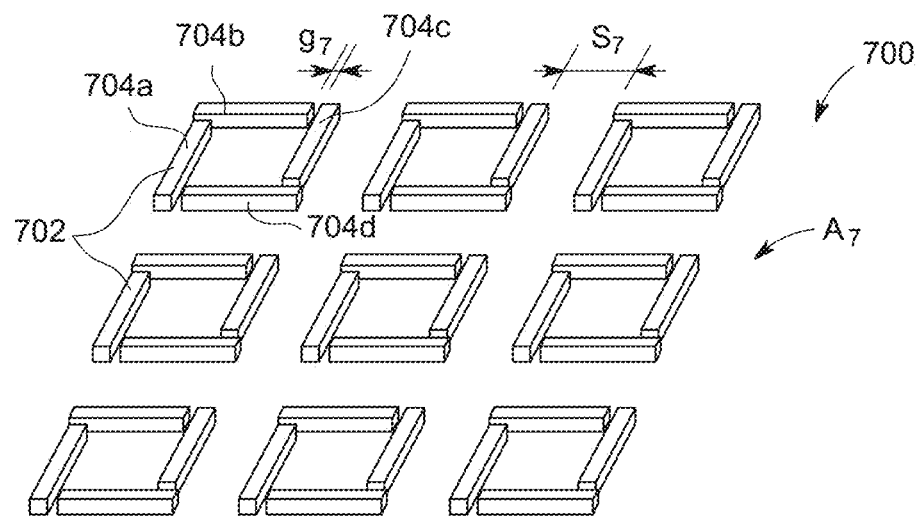
FIGS. 7A and 7B are perspective and plan views, respectively, which show yet another class of metallic structure applicable to passive components adapted for integration with active semiconductor devices, utilizing meta-material structures according to one or more embodiments.
Figure 7B:
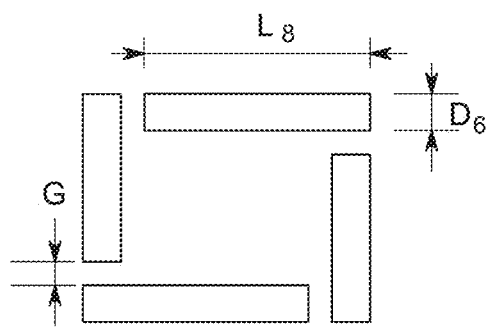

FIGS. 7A and 7B are perspective and plan views which show yet another metallic structure 700 applicable to passive components adapted for integration with active semiconductor devices. Like the preceding examples, the metallic structure 700 is especially suitable for the fabrication of on-chip optical filters. The structure 700 is referred to herein as a meta-material filter and comprises an array $A_7$ of meta-material elements.

In an embodiment, the metallic structures comprising the array $A_7$ of FIG. 7A are split ring resonators 702 formed from sections as sections 704a-704d each of which separated from its nearest neighbors by a gap G. The structures of FIGS. 7A and 7B, as well as the variants depicted in FIGS. 7C-7E, have several advantages which, in certain circumstances, make it a superior choice than previously described embodiments.

Consider the performance of the waveguide array structures described in FIGS. 1A-1D, 2A, and 2B, or the stacked gratings of FIGS. 6A and 6B. The former have extremely good performance and are very robust in filter applications where its wavelength limitations do not present an issue. In fluoroscopic detection and/or imaging situations, for example, the waveguide array is only acceptable where fluorophores having an excitation band below 600 nm and an emission band above 650 nm are applicable. While many fluorescent quantum dots aheady meet this criteria, anomaly filter configurations using stacked gratings—as exemplified by FIGS. 6A and 6B—have greater versatility (the latter are more versatile because the transmission dip is tunable by tuning structural parameters). However, this structure is not as robust for stray or scattered layer excitation light.

Metallic structures of the meta-material type advantageously deliver the desired robustness, by providing a moderate rejection of stray or scattered light robust configuration. As shown FIGS. 7A and 7B, each element of the array $A_7$ is dimensioned and arranged so that a sub-wavelength structure is obtained. The spacing $S_7$ are separated by a dimension which is generally smaller or at most comparable to the wavelength of laser acting as the excitation source.

An embodiment of a split ring resonator is shown in FIGS. 7A and 7B and consists of four copper bars forming a square ring with 4 gaps. The length $L_8$, width $D_8$, gap width G, and the metal bar thickness of the resonator are tuned and optimized in simulations to provide the desirable filter performance. The pitch of the array is generally not as important in terms of its effect on performance, but it is typically chosen so that the array is closely packed.

Figure 7C:
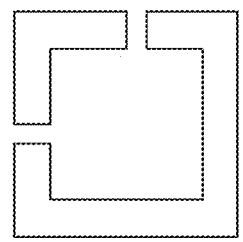
FIGS. 7C-7E are respective plan views depicting other meta-material structures according to one or more embodiments.
Figure 7D:
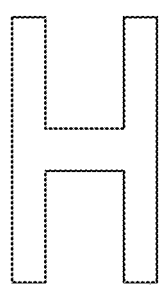
Figure 7E:
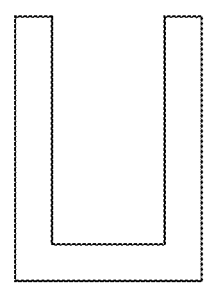
Figure 8A:
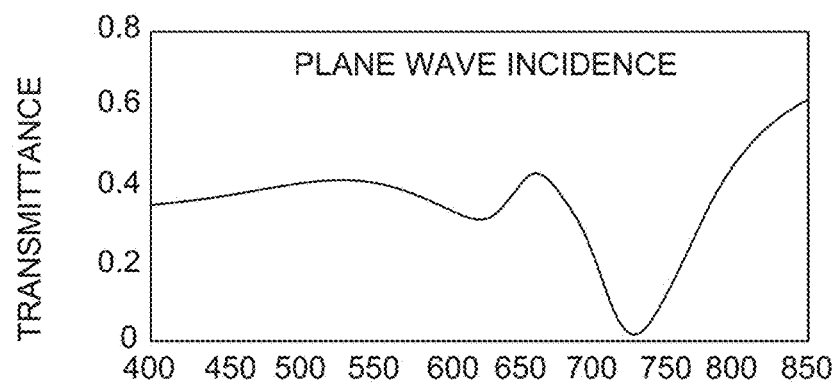
FIG. 8A to 8D are graphical representations of filter performance obtained using meta material structures according to embodiments of the present disclosure.
Figure 8B:
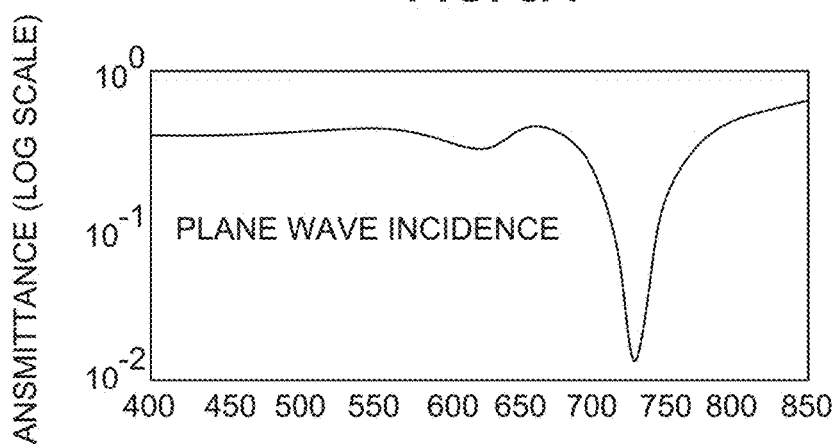
Figure 8C:
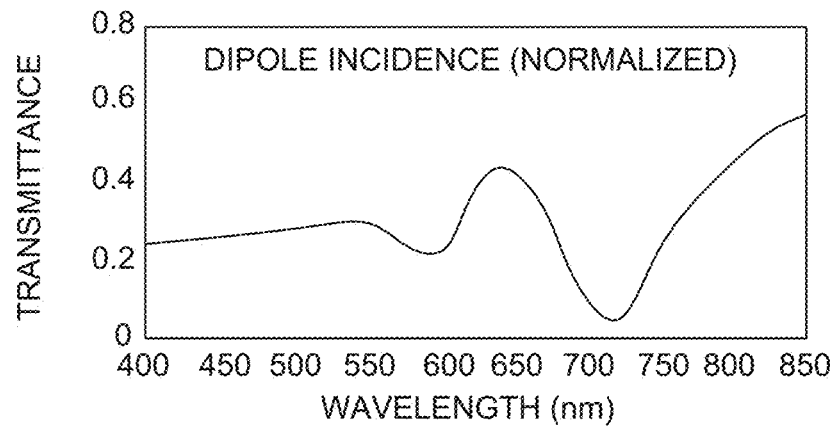
Figure 8D:
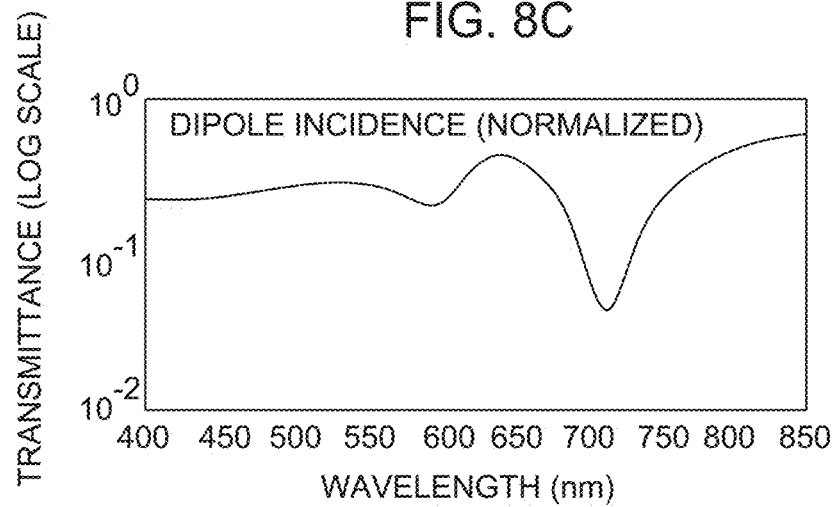

In some embodiments, the array formed by numerous single elements comprises a single layer. In other embodiments, a number of layers are stacked much like the multiple-layer structure used for the Grating Anomaly filter configurations of FIGS. 6A and 6B, the cascading of multiple layers serving to improve the filter performance with a minor penalty in the form of slightly decreased transmission efficiency at the fluorescence wavelength. FIGS. 7B through 7E depict several other architectures of the individual metallic material structures. FIGS. 7B, 7C and 7E are classical split rings, while FIG. 7F is an H-shaped resonator.

One example of the filter design for use in simulating performance utilizes the structure of FIG. 7B, which is a split ring resonator with four gaps. The outer side length of the square is 100 nm, the inner side length is 70 nm (therefore, the width of the "ring" is 15 nm), the gap width G is 20 nm, the pitch of the array is 150 nm, and the filter is embedded in the dielectric material with a refractive index of 1.5. The array is single-layer. The filter performance is shown in FIG. 8A-8D. A clear dip is shown in each of FIGS. 8A-8D within a wavelength band of around 720-730 nm. Although the rejection at the transmission dip is moderate, a distinct difference from the previous Grating Anomaly Filter (FIGS. 6A-6D) in the robustness for incident laser light or light scattered at large angles. In the Grating anomaly filter, the rejection of normal incident laser light is very high while the rejection of the oblique incident light is not (not shown). In comparison, the Meta-material filter works well even as we utilize a dipole source to simulate the oblique incidence, as shown FIG. 8. Therefore, in real applications where both directly incident (thus much stronger) and scattered laser light coexist, the two types of filters can be combined together to achieve an overall good performance.

A photosensor with greater than 50 dB filtering, at a given wavelength, can be advantageously realized through an integrated photonic-electronic co-design which enables the optical layers to be brought in close affinity to the photo detection layer. That is, the bottom via layer can be designed to touch the silicon. Consider a high performance filter on top of a photo-diode, which rejects light at a particular wavelength (in our case, ~405 nm) to a very high extent (100 dB). This means any optical leakage that allows 1 out of $10^{10}$ photons to reach the sensor will degrade the filter performance.

For optimal results, any stray light or leakage light induced by, for example, any gaps sized several microns anywhere on chip near pad, chip side, etc. or by gaps as a result of DRC rules should be eliminated. In this regard, the photonic copper structure and electronic copper wirings are part of a common layer, and applicable DRC rules may dictate a certain spacing between any adjacent metal layers.

Figure 9:
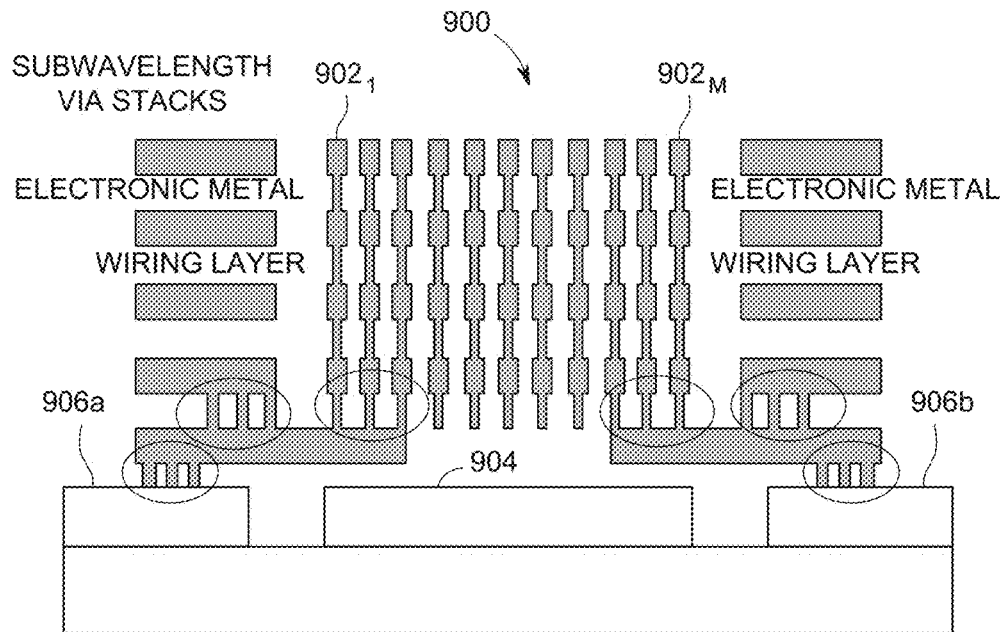
FIG. 9 is a cross sectional view depicting an integrated detecting, sensing or measuring system which integrates both passive and active optical components in a single structure, according to one or more embodiments.

According to one or more embodiments, the aforementioned issue is resolved by a "global level" metal and via layer design methodology that completely isolates the sensor from stray, scattered leakage excitation light. An embodiment of a structure integrating both passive and active optical components in a single structure through application of such a methodology is depicted in FIG. 9. If any gap must exist, the lowest metal layer with via stacks is dimensioned and arranged to seal it. This prevents light leakage from the top gap. The backside silicon (hundreds of micron thick) offers a natural optical isolation for the photon active region. Finally, from the side, "dummy" silicon layers (i.e., layers which are electronically isolated from the active region plus the lowest via layers) are used to prevent any light from leaking from the sides. For a wavelength around 405 nm (filtering wavelength and the laser excitation wavelength), a typical lateral dimension of 20 microns is typically sufficient for the dummy silicon layer to perform the sealing function.

Figure 10B:
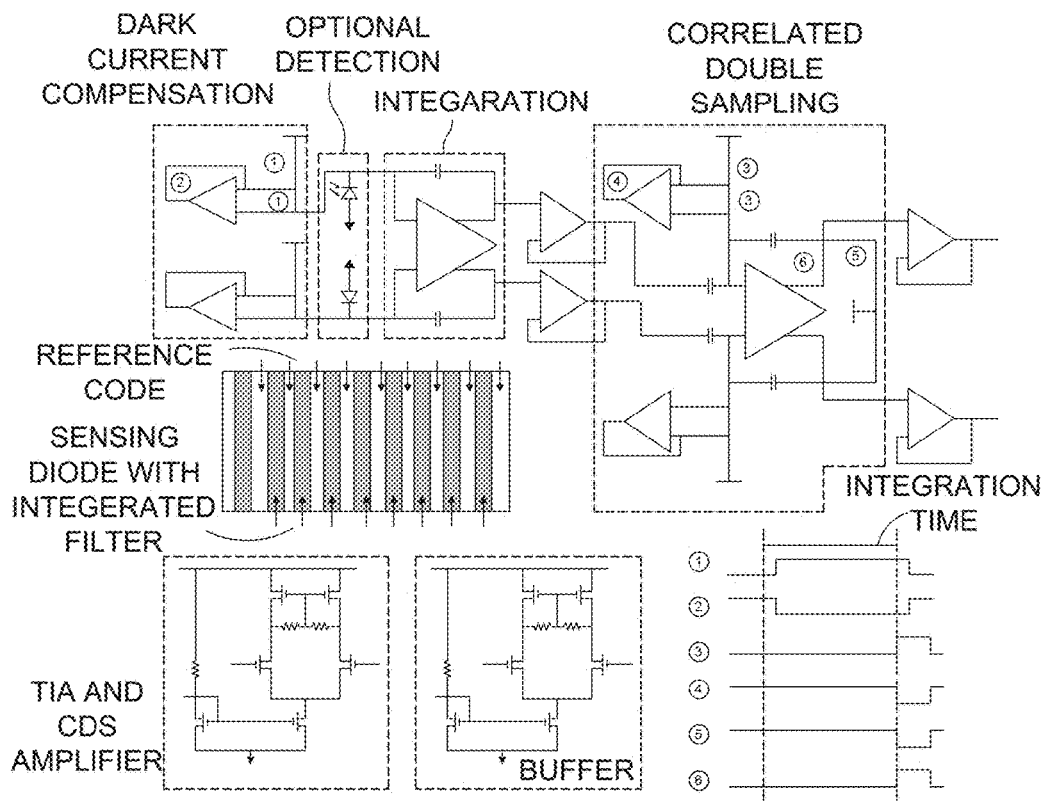
FIGS. 10A and 10B depicts schematics for an integrated photodetector architecture with dark current compensation, correlated double sampling, and microscopic view of differential diode layout, with FIG. 10B further including a timing diagram, according to one or more embodiments.
Figure 10A:
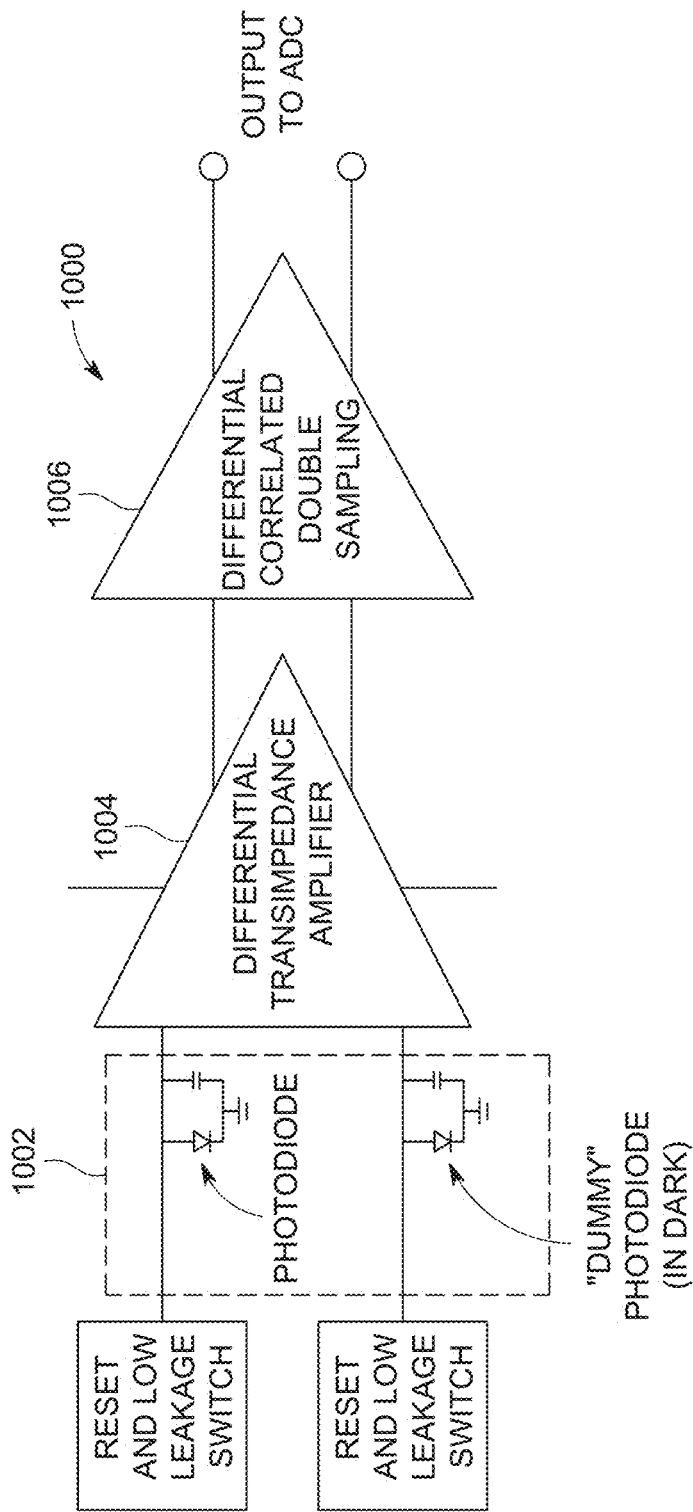

FIGS. 10A and 10B depicts a photo-detector circuit 1000 which incorporates dark current compensation suitable for use where fluorescence sensing system is designed to be performed directly on a single chip (i.e. the filters and photo-detection circuits are embedded monolithically). The photo-detection circuit is designed to transfer a weak fluorescence signal to an electrical signal. Preferably, the design is sensitive, characterized by low noise, and operates effectively over a large dynamic range. The simplified arrangement shown in FIG. 10A comprises a differential photo diode 1002, a transimpedance amplifier 1004 and a correlated double sampling circuit 1006.

In an extremely low-level light detection system, dark current not only severely limits the dynamic range of a fluorescence imaging or detection system, but it also induces non-negligible amounts of noise. In an embodiment, this issue is addressed by designing the photo-sensitive area of the photo diode to be divided alternatively into a plurality of modules—half of them form the "real" photo-detector that detects the fluorescence signal, and the other half are covered by thick metal layers to serve as a "dummy" photo diode. In operation, the dark current in the two photo diodes should be very close to each other, in accordance with the differential design. In the illustrative example of FIG. 10A, the photo-sensitive areas of the photodiode are divided into eight modules for each of the "real" and "dummy" detecting functions, respectively.

Differential transimpedance amplifier 1004 subtracts the dark current of the dummy photo diode from the real one, which serves to increase the dynamic range. The differential signal is further processed by the correlated double sampling circuits 1006 (also designed to be differential) for purposes of noise reduction. The output of the double sampling circuits is sent to external analog-to-digital converters for further process and reading.

Each sensor site comprises of a sensing diode with the nano-plasmonic filter and a reference diode which is optically shielded. The differential diode structure is laid out in an interdigitating fashion, and current compensation circuit is introduced to reduce the influence of dark current. This increasing the attainable integration time for low level light detection. As an example, a differential diode structure used in preliminary evaluation of the circuit 1000 measures 91.4 μm×123 μm. The detected signal can be amplified by a capacitive trans-impedance amplifier, operating in feedback mode which eliminates the dependency of circuit's responsivity on the diode capacitance. Correlated double sampling circuits further reduce the effect of correlated noise and offsets.

Dark current compensation mechanisms according to one or more embodiments are designed operate in the following manner. After a voltage reset at the diode node, the integration mode starts. Light induced photo-current discharges the diode capacitor that results in the voltage change at the diode node so as to be amplified and detected. However, since the diode capacitor is always leaky, which means even if the diodes (both reference and real) are in absolute dark, after the switch reset, both will discharge due to the leakage current $I_1$, which results in the voltage drop at both real and reference diode nodes. This voltage drop over time eventually will render the voltage at the diode nodes below the normal operation range of the TIA at the next stage, thus limiting the maximum allowed integration time (therefore, the detection limit). On the other hand, in the integration mode, the two switch transistors (switch 1 as shown in the figure) controlling the diodes are not completely turned off as any transistors will always have leakage current $I_2$. This leakage current essentially charges the diode to compensate for the aforementioned diode leakage; therefore, it can improve the maximum integration time. If $I_2 < I_1$, then the switch 2 is always turned off so that the minimized leakage current will be $I_1-I_2$. If $I_2>I_1$, then the switch 2 is partially turned on (controlled by its gate voltage), so that the voltage between the note at the middle of the two transistor 1 and the diode node can be controlled, this controls the leakage current from the switch 1 to diode note to below $I_2$ and close to $I_1$, therefore, the net leakage at the diode node can be minimum.

According to one or more embodiments, fully integrated CMOS on-chip fluorescence sensing and microscopy systems are implemented using passive components such as filters, wherein the filters are configured as sub-wavelength waveguide arrays, waveguide anomaly filters, or metamaterial structures. These systems overcome the deficiencies associated with traditional, nonintegrated, non-portable, bulky, and costly fluorescence sensors and microscopes. By leveraging the low cost of CMOS mass manufacturing, combining small device form factor and design for performance and convenience, the disclosed system serves as an extremely cost-effective and convenient way for fluorescence bio-sensing and microscopy as a point-of-care diagnostic tool for health monitoring and disease diagnoses.

State-of-the-art-custom CMOS imager process are mostly backside illuminated, which removes the possibility of employing the copper interconnects as optical components. Standard digital/RF CMOS processes do not have validated photo-detector models.

Figure 11:
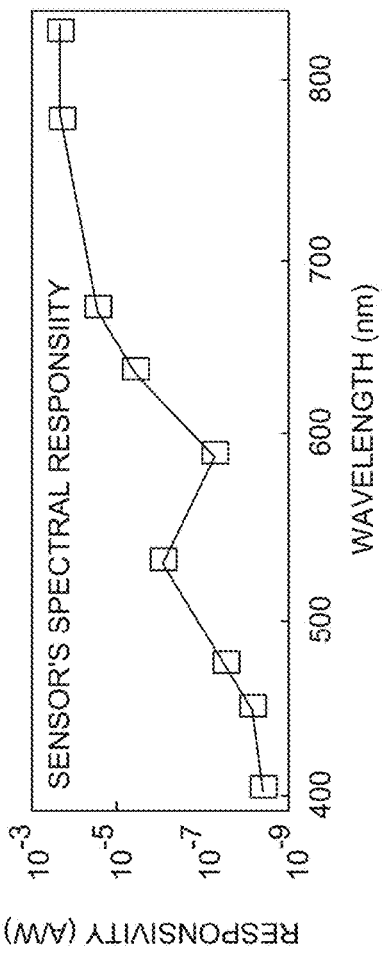
FIG. 11 and FIG. 12 are graphical representations depicting The measured spectral responsivity (405-830 nm) and the sensitivity of an integrated sensing device at an emission wavelength of around 780 nm, according to one or more embodiments.
Figure 12:
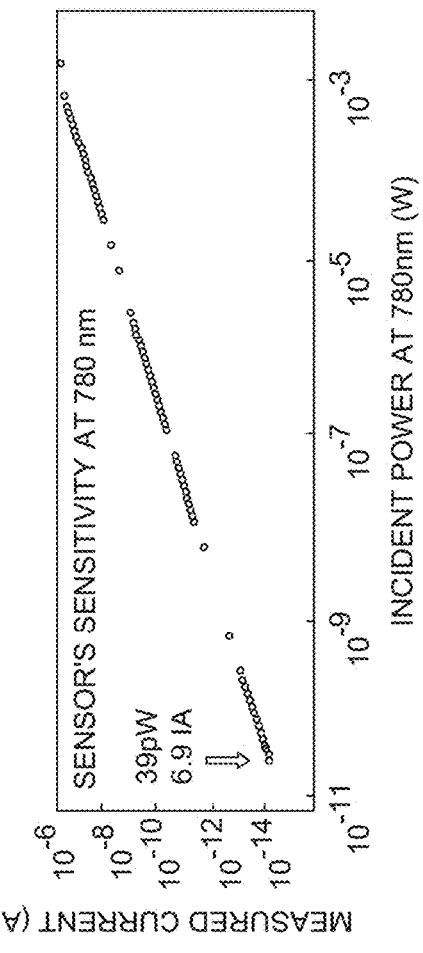

FIGS. 11 and 12 are graphical representations of sensor responsivity and sensitivity, respectively. Preliminary measurement results with different forms of diode structures (n-well/psub, p-well/n-well etc) have been carried out in a 65 nm CMOS fabrication process. A fabricated chip with integrated nano-plasmonic filter shows the lowest measured light level to be 39 pW (corresponding to 6.92 fA photo current) in 780 nm wavelength (where linearity of the chip response is still preserved. This comparatively lower than expected performance is due to the following several factors: 1) the nano-plasmonic filter itself accounts for a larger than 12 dB loss in the 780 nm region, 2) non-optimized diode structure having a much lower responsivity. If the sensitivity of the biosensor is limited by the emission filter and stray light scattering, then the minimum detectable analyte is independent of the of the diode quantum efficiency and the common loss associated in the filter. This is because both the excitation light and the fluorescence light are affected by this. The measured spectral responsivity (405-830 nm) and the sensitivity of the chip at the emission wavelength of around 780 nm are shown in FIG. 11. As expected, the responsivity resembles that of the filter and 47.6 dB filtering ratio was obtained for 405 nm excitation wavelength and 780 nm emission wavelengths. For 780 nm wavelength, highly linear response (photo current verses incidence power) was measured over 82 dB dynamic range.

An end-end design process for a fully integrated optical biosensor with an active bio-interface requires a multi-disciplinary approach. This includes preparing the interface with the bio-sample that involves functionalization of chip surface (both for DNA and proteins, for example) and sample (liquid) handling mechanism. This process has to be co-designed with the optical and electronic signal detection and processing.

Figure 13A:
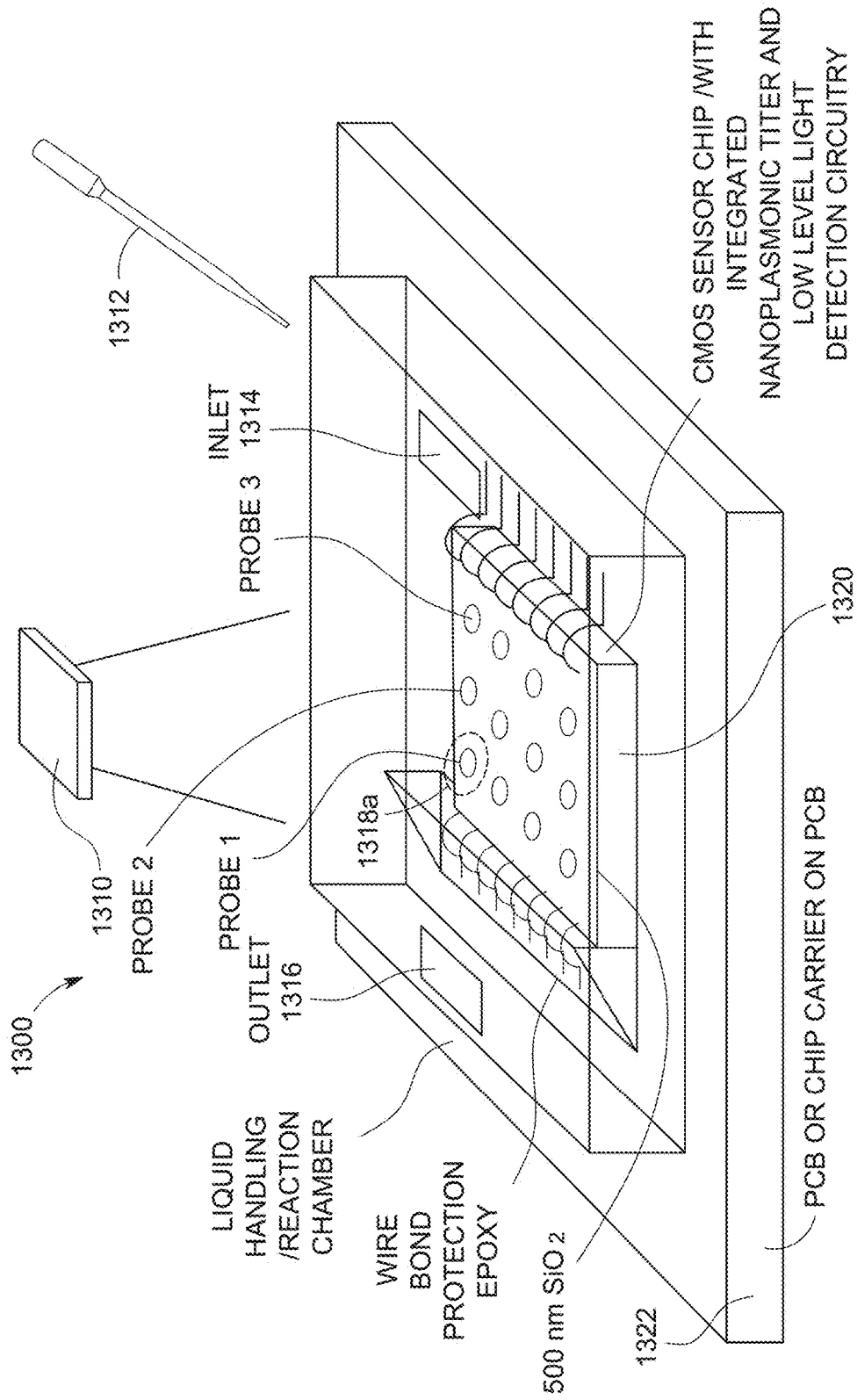
FIG. 13A is depicts a functionalized monolithically integrated chip constructed according to an embodiment of the present disclosure.

FIG. 13A depicts an illustrative fluoroscopic detection system 1300 utilizing a multiplexed chip 1302. The multiplexed chip 1302, comprising a plurality of the individual sensors 1304 described above, is functionalized with different probes at different sensor locations and the sample of interest is allowed to incubate in contact with the probe. The CMOS chip is fixed either in a chip carrier or directly on the printed circuit board using conductive epoxy (such as silver epoxy). Then the pads of the chip are wire connected using wire bonder. All pads and wires are then protected using adhesive but non-conductive materials such as silicone (PDMS), this step is to prevent any conductive liquid during the bio-assay process to short the chip by connecting different pads or wires. After the pads and wires are protected, a liquid handling chamber made of either glass of plastics is placed. This chamber could either be custom made or a ring shaped glass/plastic to hold the liquid. In the case that the chip is placed on the chip carrier then the chip carrier on PCB, the chip carrier along with the chip, the liquid handling chamber is used in the form of a cartridge, which can be replaced or disposed of after the detection mechanism.

FIG. 13B depicts a monolithically integrated fluorescence imaging system 1300' constructed according to a conventional semiconductor device fabrication technique such, for example, as CMOS processing. In the exemplary arrangement of FIG. 13B, the system 1300' comprises an array 1340 of individual copper light guides 1342, which array is dimensioned and arranged directly above an array 1350 of CMOS photo-detectors (image sensor) 1352.

Typically, the individual pixel size of each CMOS image sensor 1352 is from about 2 to about 10 microns, depending on the CMOS process and design. The light guides 1342 are of similar dimensions. In an embodiment, each light guide is fabricated from copper and has a rectangular cross sectional profile, which may or may not be a square cross-section as suggested in FIG. 13B.

The wall thickness of each light guide 1342 is typically thin (i.e., on the order of 100 nm). In many commercial scale CMOS fabrication processes, nominal dimensions such as these may not be practical to fabricate. Modification of the design may be necessary to approximate and/or emulate an idealized "hollow waveguide".

In a CMOS process where a via layer of 100 nm×100 nm cross section is a design limitation, and the array pitch is likewise 100 nm, sub-wavelength metallic structures can be directly used to implement thin wall "hollow waveguide", since the sub-wavelength design characteristically prevents photons in one light guide from leaking to an adjacent structure. In addition, the light guide needs to be as close to the image sensor 1352 and bio sample as possible—the bio sample for imaging is prepared directly on the top of the chip. Nonetheless there is still spacing between the sample and the light guide, which would result in the image blurring (similar argument holds for the spacing between light guide and photo detector). Finally, robust optical filters such as the sub-wavelength copper plasmonic waveguide array and substrate based metamaterial filters can be directly incorporated in the light guide. In the exemplary embodiment of FIG. 13B, a spectral filter comprising an array of sub-wavelength copper plasmonic waveguides 1345 (only one row of which is shown). The respective arrays of light guides 1342, sub-wavelength copper plasmonic waveguides 1345, and sensors 1352 are fabricated according to conventional CMOS techniques using, in an embodiment, a silicon-based material system. Other semiconductor material systems, with which spectral filters and other passive components fabricated in accordance with the present disclosure are especially adapted for integration with sensing, detecting or imaging devices fabricated from those materials include GaAs, InP, and InGaAsP depending upon the nature of the application.

As such, the monolithically integrated structure 1310 can directly function as an imaging system. In embodiments, the spatial resolution of an image is primarily determined by the pixel pitch, and is generally, two to three times the pitch. Since a 2-3 micron pixel pitch is common in today's CMOS image sensor designs, a spatial resolution could be on the order of from about four to about nine microns. This moderate resolution is believed by the inventors herein to be sufficient for many fluorescence imaging applications.

Figure 13C:
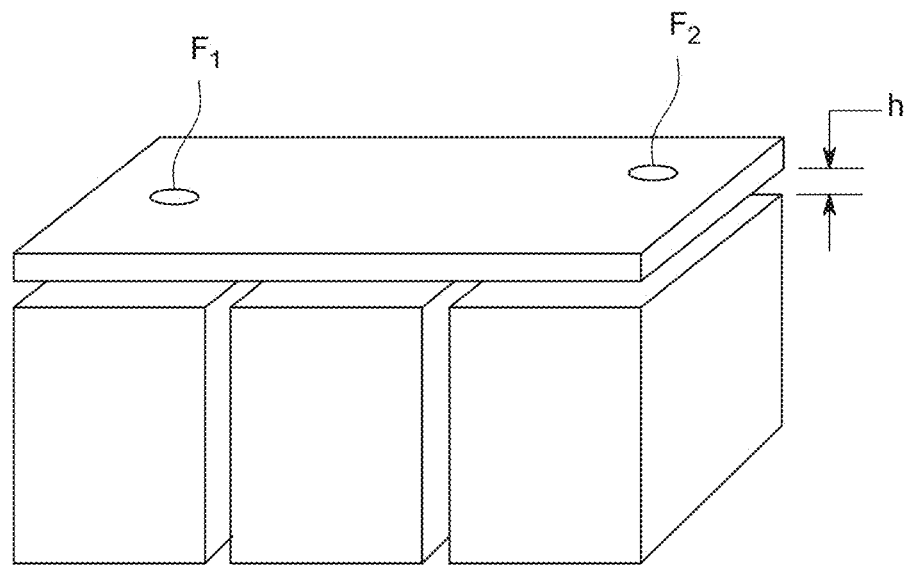
FIGS. 13C and 13D depict the separation between a sample under fluoroscopic investigation and an imaging plane, according to one or more embodiments.
Figure 13D:
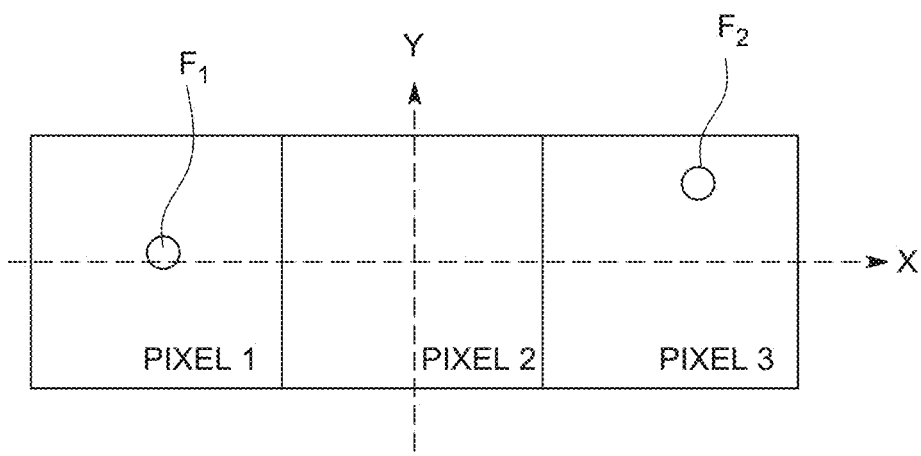

FIGS. 13C and 13D depict the separation between a sample under fluoroscopic investigation and an imaging plane, according to one or more embodiments. With reference to FIG. 13B, the estimation and analysis of the effect of the spacing h between the bio sample plane (also the fluorophore plane) and the light guide array on the imaging resolution will now be described with reference to the need to distinguish between a pair of fluorophores with 3 pixels in a row, where fluorophore $F_1$ and $F_2$ are each located within the boundary of pixel $P_1$ and $P_3$, respectively.

Where h is close to zero, then almost all the radiation by fluorophore $F_1$ and $F_2$ enters the pixel $P_1$ and $P_3$, respectively (i.e., no light is captured by pixel 2). This means that the two fluorophores are clearly distinguishable (pixel $P_1$ and $P_3$ are each detecting light while pixel $P_2$ remains dark). A more complex question is the effect of a nonzero value of h on imaging resolution. Expressing the problem differently, if one desires to use three pixels to distinguish two point sources, what is the maximum h allowed?

Since the imaging resolution depends on various factors including the exact positions of the two fluorophores, assumptions can be made during the modeling process of the estimation. For purposes of analysis, it can be assumed (1) that the fluorophores are isotropic point sources with equal radiation strength, (2) that the efficiency of the light guide for light with different incident angles are essentially the same, and (3) that all the light at the end of the light guided are collected by the con responding photo detectors underneath (no crosstalk between the light guide and the photo detector).

Fixing the fluorophore $F_1$ at the center of the pixel $P_1$ and changing the position of the fluorophore $F_2$ (within the boundary of pixel $P_3$), the requirement for the maximum h can be identified. The limiting criterion is set that if the total light intensity at the pixel $P_2$ is no more than half of the total intensity at either pixel $P_1$ or pixel $P_3$, then the two fluorophores are distinguishable from one another. In the extreme condition where fluorophore $F_2$ is very close to the boundary of pixel $P_2$ and $P_3$, $h_{max}$ must be very close to zero, but generally, $h<0.3L$ is a sufficient condition for fluorophores at most locations.

Figure 14:
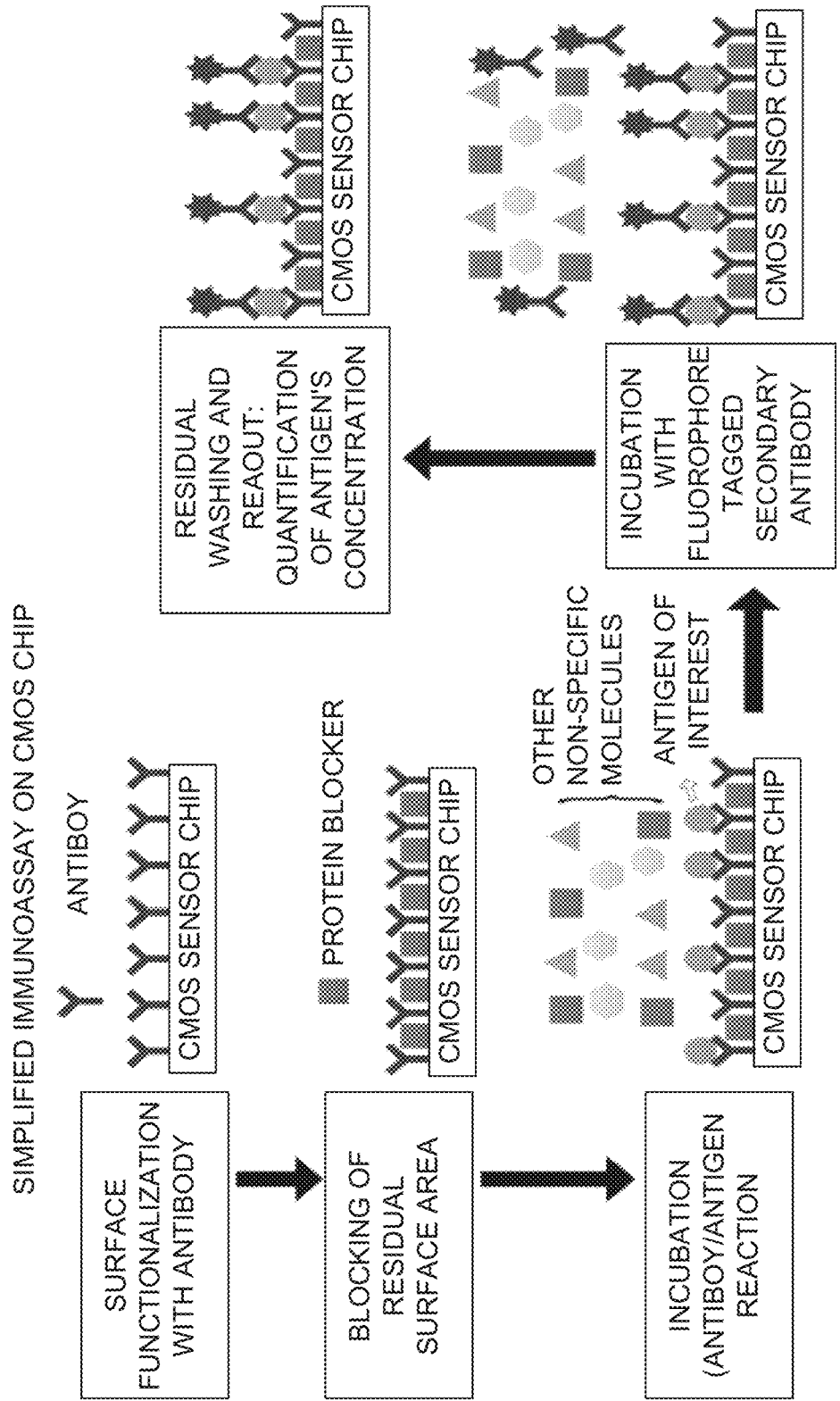
FIG. 14 is a perspective view depicting processes of chip surface functionalization and affinity reaction for an antigen/antibody assay, according to one or more embodiments.

FIG. 14 depicts the implementation of a sandwich assay protocol on the surface of a CMOS sensor chip 1402 according to an embodiment. While the sensor could be prepared for detection of either nucleic acid or proteins, an example of an antibody/antigen detection is demonstrated in FIG. 14. In an embodiment, a 1-2 µm layer of $Si_{O2}$ is deposited to the silicon-nitride surface of the chip using chemical vapor deposition (CVD) method. To ensure a good deposition within a low temperature, PECVD is typically used. The deposition also reduces surface roughness. Then, a protocol for functionalization of glass surface is followed. An epoxy surface or silianization of the $Si_{O2}$ is prepared to allow the capture antibody to be covalently bonded to the surface. The rest of the surface is then blocked to minimize non-specific binding. In order to form different probes at different sensing sites, a spotter (such as those used in the DNA microarray) is used to deposit different probes on different sites.

After the functionalization and probe forming, the chip is incubated with the analyte of interest so that mostly the specific antigen of interest is captured by the surface. The rest of the solution along with the nonspecific molecules is washed away (using the inlet and outlet of the liquid handling chamber) and the antigen is detected using a fluorescence-labeled secondary antibody (could be the same probe on the surface). When the assay is illuminated with an inexpensive diode laser or LED source, the light emitted from the tags is guided through the nanophotonic structures and detected by the photodetectors.

Figure 15:
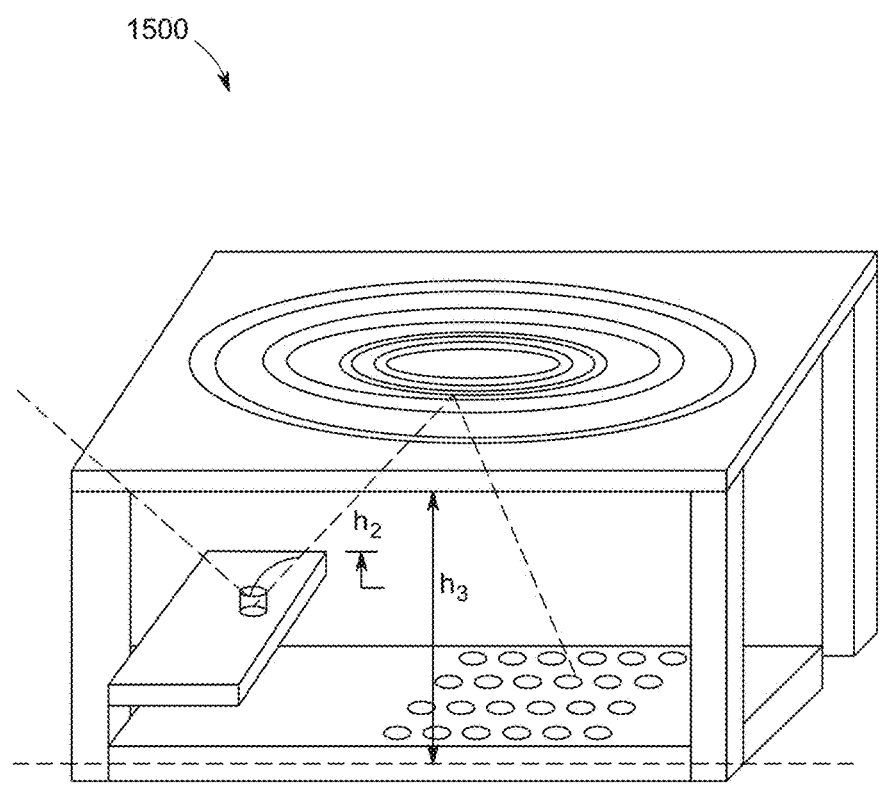
FIG. 15 is a perspective view depicting a double chip fluorescence microscopy system according to one or more embodiments.

FIG. 15 is a perspective view depicting a double chip fluorescence microscopy system 1500 according to one or more embodiments. A design procedure for the system 1500 includes a mechanical stage, which can be cost-effectively made via techniques such as 3D printing, by which two CMOS chips are mounted to support the bio-sample. A lower substrate (e.g., a first chip) 1502 serves as the detector array (image sensors) for microscopy, while a upper substrate 1504 (i.e., a second chip) includes a lens 1506. The upper substrate is supported by supports 1508, to which is secured a sample receiving tray 1509.

The lens 1506 works in reflection mode for imaging and magnification, with optimized design to eliminate various imaging aberrations. When the bio sample is illuminated by an external laser (not shown), the fluorescence image is reflected, magnified, and imaged by the CMOS metallic lens to the lower substrate, and resolved and recorded by an array of high-sensitivity photo-detectors. Since even in this configuration, astray or scattered laser excitation light is often inevitable, a fully integrated filter as described previously is again used to keep the laser excitation signal away from the weak fluorescence signal.

In an embodiment, the lens 1506 of fluorescence microscopy system 1500 is an enhanced Fresnel lens. In some embodiments, the lens is a metallic structure comprising either a series of concentric rings of wire, or a series of arcuate or curved wire segments. Since wire is a commonly used component in many device fabrications processes, such lens configurations are inexpensive to manufacture—requiring little to no modification of existing semiconductor device processing and fabricating equipment. Where an oxidizable metal such as copper, aluminum or silver is used, the lens may be encapsulated with a dear, dielectric material index matched to the application. Alternatively, a noble metal such as gold or platinum may be used.

Working in the reflection mode (where the light reflected from the metal wring interferes and focuses), the lens can be compatibly manufactured (no post fabrication is required), and offers compact system f01m factor. More importantly, the CMOS nanometer-scale resolution offers unparalleled advantages to design and optimize the Fresnel lens to eliminate aberrations as much as possible. Two stages of design are proposed. First of all, the Fresnel lens is designed to have a fixed imaging feature, specifically, this means that the lens is designed in the framework of diffraction optics so that the imaging of the central point of the object is "theoretically perfect", with no approximations made. Such design greatly improves the imaging quality of the Fresnel lens. Furthermore, conventional aberration correction techniques can be used to further improve the imaging quality, especially for multi-wavelength imaging as well as off-axis imaging.

Light (e.g. from a laser source, not shown) is directed at the sample 1510, which may be a bio-sample or a chemical sample, placed on tray 1512. The light is then reflected by the sample and strikes lens 1506 which, in turn, reflects that light toward the pixels of the sensor array of lower substrate 1502 for detection, sensing and/or imaging according to one or more embodiments.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present disclosure and its practical applications, to thereby enable others skilled in the art to best utilize the invention and various embodiments with various modifications as may be suited to the particular use contemplated.

All examples described herein are presented in a non-limiting manner. Various modifications and changes may be made as would be obvious to a person skilled in the art having benefit of this disclosure. Realizations in accordance with embodiments have been described in the context of particular embodiments. These embodiments are meant to be illustrative and not limiting. Many variations, modifications, additions, and improvements are possible. Accordingly, plural instances may be provided for components described herein as a single instance. Boundaries between various components are somewhat arbitrary, and particular structures and combinations of elements are illustrated in the context of specific illustrative configurations. Other allocations of functionality are envisioned and may fall within the scope of claims that follow. Finally, structures and functionality presented as discrete components in the example configurations may be implemented as a combined structure or component. These and other variations, modifications, additions, and improvements may fall within the scope of embodiments as defined in the claims that follow.

While the foregoing is directed to embodiments of the present invention, other and further embodiments of the invention may be devised without departing from the basic scope thereof, and the scope thereof is determined by the claims that follow.

The invention claimed is:

1. A passive component for filtering light, comprising:
a plurality of metallic nanostructures arranged as an array of structures to filter light incident upon the array of structures,
wherein each of the plurality of metallic nanostructures is dimensioned and arranged in the array of structures to be within a path of light as the light attempts to propagate through the passive component, and wherein at least a portion of the plurality of metallic nanostructures is made from a selected material such that light of specific wavelengths or a range of wavelengths propagates more efficiently through the passive component than light of other wavelengths.

2. The passive component of claim 1, wherein the array is an m×n array and m or n is an integer greater than 1.

3. The passive component of claim 2, wherein the array has uniform spacing between each of the plurality of metallic nanostructures.

4. The passive component of claim 1, wherein each of the plurality of metallic nanostructures has a thickness of approximately 100 nm and a length of approximately 1 or 2 microns.

5. The passive component of claim 4, wherein the spacing between nanostructures in the plurality of metallic nanostructures is approximately 100 nm.

6. The passive component of claim 4, wherein the spacing between nanostructures in the plurality of metallic nanostructures is approximately 130 nm.

7. The passive component of claim 1, wherein the plurality of metallic nanostructures comprises a meta material structure, the meta material structure comprising at least one slotted resonator.

8. The passive component according to claim 1, wherein the plurality of metallic nanostructures serves as a grating.

9. The passive component according to claim 8, wherein the grating is fabricated as a metal embedded in a dielectric layer.

10. The passive component of claim 1, wherein each of the metallic nanostructures has an approximate thickness less than 100 nm.

11. The passive component of claim 1, wherein the light of specific wavelengths or the range of wavelengths that propagates more efficiently passed the plurality of metallic nanostructures is defined by at least a material composition of the plurality of metallic nanostructures.

12. The passive component of claim 1, wherein the light of specific wavelengths or the range of wavelengths that propagates more efficiently passed the plurality of metallic nanostructures is defined by at least one of a geometry of the plurality of metallic nanostructures or the arrangement of the plurality of metallic nanostructures within the array.

13. A passive component for filtering light, comprising:
a plurality of metallic nanostructures arranged as an array of structures,
wherein each of the plurality of metallic nanostructures is dimensioned and arranged in the array to be within a path of light as the light propagates, such that light of specific wavelengths or a range of wavelengths propagates more efficiently passed the plurality of metallic nanostructures than light of other wavelengths, and
wherein each of the plurality of metallic nanostructures has a thickness of approximately 100 nm and a length of approximately 1 or 2 microns.

14. The passive component of claim 13, wherein the array has uniform spacing between each of the plurality of metallic nanostructures.

15. The passive component of claim 13, wherein the plurality of metallic nanostructures comprises a meta material structure, the meta material structure comprising at least one slotted resonator.

16. The passive component of claim 13, wherein the light of specific wavelengths or the range of wavelengths that propagates more efficiently passed the plurality of metallic nanostructures is defined by at least one of a geometry of the plurality of metallic nanostructures or the arrangement of the plurality of metallic nanostructures within the array.

17. A passive component for filtering light, comprising:
a plurality of metallic nanostructures arranged as an array of structures,
wherein each of the plurality of metallic nanostructures is dimensioned and arranged in the array to be within a path of light as the light propagates, such that light of specific wavelengths or a range of wavelengths propagates more efficiently passed the plurality of metallic nanostructures than light of other wavelengths, and wherein each of the metallic nanostructures has an approximate thickness less than 100 nm.

18. The passive component of claim 17, wherein the array has uniform spacing between each of the plurality of metallic nanostructures.

19. The passive component of claim 17, wherein the plurality of metallic nanostructures comprises a meta material structure, the meta material structure comprising at least one slotted resonator.

20. The passive component of claim 17, wherein the light of specific wavelengths or the range of wavelengths that propagates more efficiently passed the plurality of metallic nanostructures is defined by at least one of a geometry of the plurality of metallic nanostructures or the arrangement of the plurality of metallic nanostructures within the array.

* * * * *